United States Patent
Turner et al.

(10) Patent No.: US 12,404,434 B2
(45) Date of Patent: Sep. 2, 2025

(54) ABSORBENT ARTICLES COMPRISING A SBC BASED HOTMELT ADHESIVE

(71) Applicant: The Procter & Gamble Company, Cincinnati, OH (US)

(72) Inventors: Robert Haines Turner, Cincinnati, OH (US); Torsten Lindner, Kronberg (DE); Christian Neu, Eppstein (DE); Gabriele Stiehl, Bad Soden (DE); Jeremia Schwabe, Gersthofen (DE); Erik Hauck, Gersthofen (DE); Felix Kirschvink, Frankfurt (DE); Sebastijan Bach, Charlotte, NC (US)

(73) Assignee: The Procter & Gambel Company, Cincinnati, OH (US)

( * ) Notice: Subject to any disclaimer, the term of this patent is extended or adjusted under 35 U.S.C. 154(b) by 356 days.

(21) Appl. No.: 17/151,749

(22) Filed: Jan. 19, 2021

(65) Prior Publication Data
US 2021/0230464 A1  Jul. 29, 2021

Related U.S. Application Data

(60) Provisional application No. 62/966,140, filed on Jan. 27, 2020.

(51) Int. Cl.
*C09J 153/02* (2006.01)
*A61F 13/58* (2006.01)
*C09J 7/35* (2018.01)

(52) U.S. Cl.
CPC .......... *C09J 153/025* (2013.01); *A61F 13/58* (2013.01); *C09J 7/35* (2018.01); *C09J 2203/358* (2020.08)

(58) Field of Classification Search
CPC .... C09J 153/025; C09J 7/35; C09J 2203/358; A61F 13/58
See application file for complete search history.

(56) References Cited

U.S. PATENT DOCUMENTS 5,026,756 A   6/1991   Arendt
5,599,335 A   2/1997   Goldman
(Continued)

FOREIGN PATENT DOCUMENTS

EP   1447067 B1   12/2007
EP   1447066 B1   10/2008
(Continued)

OTHER PUBLICATIONS

Extended European Search Report and Search Opinion; Application No. 21152344.4; dated Apr. 23, 2021; 6 pages.

*Primary Examiner* — Kai H Weng
*Assistant Examiner* — Kate Elizabeth Strachan
(74) *Attorney, Agent, or Firm* — Anna E. Haller; Angela K. Haughey; Daniel S. Albrecht

(57) ABSTRACT

An absorbent article comprising a hotmelt adhesive comprising a styrene-block-copolymer (SBC), an amorphous polyolefin and optionally a tackifier. The SBC is preferably selected from the group of SEBS, SEPS and SEP polymers, and the amorphous polyolefin is preferably a propylene-based copolymer (PbP) having a weight-average molecular weight Mw of less than 10 000 g/mol. The hotmelt adhesive bonds two components of the article, for example SAP particles on the core wrap.

19 Claims, 5 Drawing Sheets

(56) References Cited

U.S. PATENT DOCUMENTS

| | | | |
|---|---|---|---|
| 5,836,930 A * | 11/1998 | Lantz | A61F 13/511 |
| | | | 604/389 |
| 6,030,373 A * | 2/2000 | VanGompel | A61F 13/58 |
| | | | 604/389 |
| 6,645,190 B1 | 11/2003 | Olson | |
| 6,761,711 B1 | 7/2004 | Fletcher | |
| 6,767,424 B1 † | 7/2004 | Butterbach | |
| 6,817,994 B2 | 11/2004 | Coenen | |
| 6,840,928 B2 | 1/2005 | Datta | |
| 6,849,067 B2 | 2/2005 | Fletcher | |
| 6,893,426 B1 | 5/2005 | Coenen | |
| 6,953,452 B2 | 10/2005 | Coenen | |
| 6,969,377 B2 | 11/2005 | Koele | |
| 7,156,833 B2 | 1/2007 | Couture-Dorschner | |
| 7,201,744 B2 | 4/2007 | Van Gompel | |
| 7,497,851 B2 | 3/2009 | Koele | |
| 7,682,349 B2 | 3/2010 | Coenen | |
| 7,744,576 B2 | 6/2010 | Busam | |
| 7,862,550 B2 | 1/2011 | Koele | |
| 8,007,485 B2 | 8/2011 | Coenen | |
| 8,361,048 B2 | 1/2013 | Kuen | |
| 8,372,052 B2 | 2/2013 | Coenen | |
| 8,579,876 B2 | 11/2013 | Coenen | |
| 8,614,271 B2 † | 12/2013 | Davis | |
| 8,747,379 B2 | 6/2014 | Fletcher | |
| 9,499,727 B2 * | 11/2016 | Golombowski | C08G 18/2081 |
| 9,879,160 B2 * | 1/2018 | Schroeyers | C09J 123/14 |
| 9,982,098 B2 † | 5/2018 | Sustic | |
| 2006/0024433 A1 | 2/2006 | Blessing | |
| 2008/0312617 A1 | 12/2008 | Hundorf | |
| 2008/0312622 A1 | 12/2008 | Hundorf | |
| 2010/0051166 A1 | 3/2010 | Hundorf | |
| 2010/0204407 A1 * | 8/2010 | Bouquet | C08F 4/56 |
| | | | 526/89 |
| 2011/0250413 A1 | 10/2011 | Lu | |
| 2011/0268932 A1 | 11/2011 | Catalan | |
| 2011/0319848 A1 | 12/2011 | Mckiernan | |
| 2012/0312491 A1 | 12/2012 | Jackels | |
| 2014/0072767 A1 | 3/2014 | Klaska | |
| 2014/0358100 A1 | 12/2014 | Remmers | |
| 2017/0252226 A1 * | 9/2017 | Arizti | A61F 13/42 |
| 2018/0334597 A1 * | 11/2018 | Eichler-Johnson | C09J 165/00 |
| 2019/0292361 A1 | 9/2019 | Flood | |
| 2019/0382631 A1 * | 12/2019 | Gu | C09J 123/142 |
| 2020/0030162 A1 * | 1/2020 | Lindner | A61F 13/45 |
| 2021/0147726 A1 * | 5/2021 | Schwabe | C08F 210/06 |

FOREIGN PATENT DOCUMENTS

| | | | |
|---|---|---|---|
| EP | 1621165 B1 | 4/2010 | |
| EP | 2905000 B1 | 12/2016 | |
| EP | 2905001 B1 | 1/2017 | |
| EP | 3271436 B1 | 8/2019 | |
| WO | 9511652 A1 | 5/1995 | |
| WO | 9513332 A1 | 5/1995 | |
| WO | 2006020309 A1 | 2/2006 | |
| WO | 2012052172 A1 | 4/2012 | |
| WO | 2012170778 A1 | 12/2012 | |
| WO | 2012170798 A1 | 12/2012 | |
| WO | 2014093323 A1 | 6/2014 | |
| WO | 2014194074 A1 | 12/2014 | |
| WO | 2015031225 A1 | 3/2015 | |
| WO | 2015183669 A1 | 12/2015 | |
| WO | 2016133712 A1 | 8/2016 | |
| WO | 2016149252 A1 | 9/2016 | |
| WO | 2016153663 A1 | 9/2016 | |
| WO | 2017132119 A1 | 8/2017 | |
| WO | 2017173894 A1 | 10/2017 | |
| WO | 2018073088 A1 | 4/2018 | |
| WO | 2019126982 A1 † | 7/2019 | |

* cited by examiner
† cited by third party

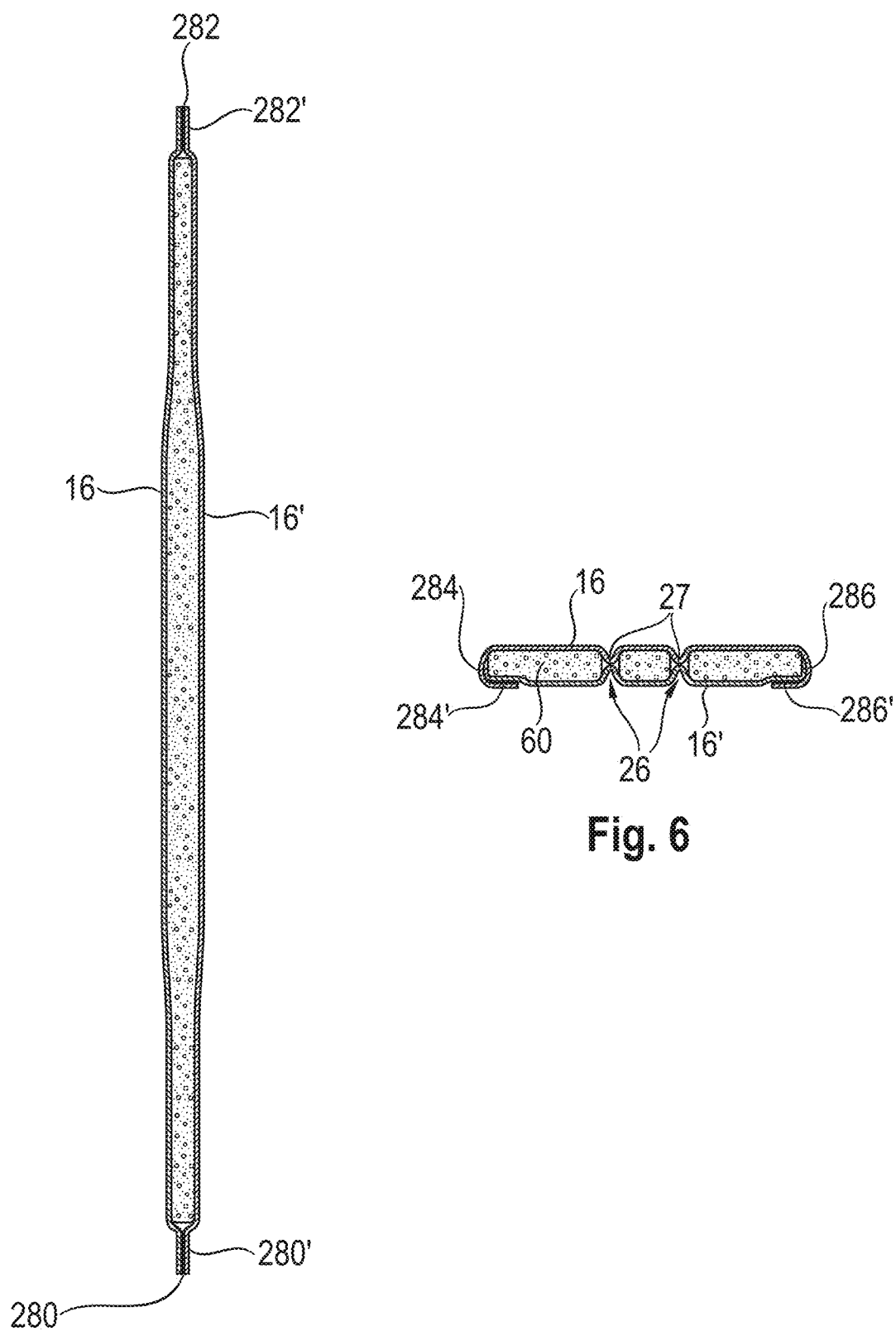

ABSORBENT ARTICLES COMPRISING A SBC BASED HOTMELT ADHESIVE

CROSS REFERENCE TO RELATED APPLICATIONS

This application claims the benefit, under 35 U.S.C. § 119(e), of U.S. Provisional Patent Application Ser. No. 62/966,140, filed on Jan. 27, 2020, the entire disclosure of which is incorporated by reference herein.

FIELD

The invention relates to personal hygiene absorbent articles such as diapers comprising a hotmelt adhesive. The hotmelt adhesive comprises a styrene-block-copolymer (SBC) and an amorphous polyolefin such as a propylene-based polymer (PbP). The hotmelt adhesive may be used to immobilize superabsorbent particles on a substrate, such as a nonwoven core wrap layer. The hotmelt adhesive may also be used as a construction glue to bond two components of a personal hygiene absorbent articles, in particular to realize a nonwoven-nonwoven bond or a nonwoven-film bond.

BACKGROUND

Disposable personal hygiene absorbent articles such as diapers, training pants and adult incontinence articles are designed for receiving and retaining bodily discharges such as urine or feces from incontinent persons. Such absorbent articles comprise a liquid pervious topsheet that faces towards the wearer's body, a liquid impervious backsheet that faces externally and an absorbent core interposed between the topsheet and the backsheet. Other components are typically present in absorbent articles, such as fluid acquisition and/or distribution layers, inner and outer barrier leg cuffs, elastics, core wraps, etc. All these components must be directly or indirectly bonded to each other. Some layers may also be folded to form a cuff or a core wrap, and thus also require bonding to themselves. While thermo-bonding or ultrasonic bonding is increasingly used in the industry, these non-adhesive bonding methods require higher basis weight material and cannot be used for continuous bonding over large area. Thus, adhesive bonding of a variety of substrates will remain in usage for absorbent articles in the future.

Hotmelt adhesives are thermoplastic compositions solid at room temperature. When heated, they are converted into the liquid or molten state—the hotmelt adhesive is in the "open" state—and can be applied to a substrate by contact or spray application. When a second substrate is applied to the hotmelt adhesive before it has re-cooled to the solid state, an adhesive bond between the two substrates is then formed. The hotmelt adhesive has an open time optimized for the intended use and effects permanent adhesive bonding of the adherends. Conventional hotmelt adhesives typically contain a cohesive base polymer, an adhesive tackifier and optionally waxes, plasticizers (oils) and further additives. Typical hotmelt adhesives and their function are described in U.S. Pat. No. 5,026,756 (Arendt) for example.

Cohesive base polymers that have been used include natural and synthetic rubbers, polyacrylates, polyisobutylenes, polyolefin(s), polyesters, polychloroprenes, polyvinyl ethers, polyurethanes, styrene block copolymers (SBC) comprising styrene-butadiene-styrene (SBS), styrene-isoprene-styrene (SIS), styrene-isoprene-butadiene-styrene (SIBS), styrene-ethylene-butadiene-styrene (SEBS), styrene-ethylene-propylene (SEP) or styrene-ethylene-propylene-styrene (SEPS) block copolymers. These base polymers are generally responsible for the cohesive effect of the adhesive system.

The processing of hotmelt adhesives, in particular application to the relevant substrates, may be realized via diverse methods, for example by spraying, extrusion-application, application by means of a roller, a bead or a slot die. In order to be optimally suitable for the wide variety of application methods the hotmelt adhesive must have rheological properties appropriate to the application method.

Plasticizer are used in hotmelt adhesive formulations to bring about viscosity reduction of the adhesive composition and thus improves its processability and ease of application. Hotmelt adhesives, particularly those based on SBC, generally contain mineral oils as plasticizers, in some cases in considerable amounts. Some mineral oils may cause an undesirable odor and may migrate into the bulk or on the surface of adjacent substrates, leading to degradation of the adhesive bond, or impairing the functionality of other components of the diaper, e.g. an oil film would reduce the effectivity of SAP. Mineral oils are preferably avoided for personal hygiene applications.

Hotmelt adhesive spray-application is a commonly used application technique. In spin-spraying a melt thread exits a spray nozzle, is optionally extended by an air stream without tearing off and is then deposited on a substrate in a spiral pattern. The application temperatures are 150° C. to 250° C. depending on the material. Conventional hotmelt adhesive formulations based on SBCs but also polyolefins are difficult to spray at temperatures of 160° C. or lower. Poor spray patterns result and severely limit the field of use. Higher application temperatures result in increased energy consumption and premature ageing of the adhesive resulting in mechanical detriments.

EP 3,271,436 (Henkel) discloses a polyolefin-based sprayable hotmelt adhesive and absorbent articles containing the adhesive. The polyolefin-based sprayable hotmelt adhesive is indicated to be particularly suitable for spraying at low application temperatures. The sprayable hotmelt adhesives having a low application temperature allow thin adhesive bonds for heat-sensitive substrates. This document does not discuss the mechanical properties of the hotmelt adhesive.

Sprayable hotmelt adhesives are typically low viscosity compositions, so that they can be applied using this application technique. They are optimized to ensure the most homogeneous and thus material-efficient coating of the substrate to be adhesively bonded. The low melt viscosity of a sprayable hotmelt adhesive is normally associated with inadequate mechanical properties which negatively affect the cohesive properties of the material. These include in particular properties such as the elongation at break, restoring force or strength of the material. Substrates adhesively bonded by spray applications usually withstand only low mechanical stresses. The adhesive bonding of the substrates is the priority while, by contrast, the cohesive polymer is intended to ensure sufficient stability to prevent the adhesive bond per se from becoming brittle. The elasticity of the adhesive bond plays only a secondary role. While hotmelt adhesives having a higher melt viscosity can be made sprayable by increasing the application temperature, such a temperature increase results in elevated energy consumption and can lead to undesired thermally induced degradation of the components used.

The possibility of formulating sprayable hotmelt adhesives based on polyolefins with SBC components is known from the prior art. WO 95/13332 (3M) describes sprayable hotmelt adhesive compositions comprising (A) styrene block copolymers, (B) tackifying resin and (C) ethylene copolymer that may be used in absorbent articles. Preferred ethylene copolymers useful in this reference are copolymers of ethylene and vinyl acetate, methyl acrylate, n-butyl acrylate, or combinations thereof.

WO 2006/020309 (Exxon) discloses polymeric composition including at least one component which is a polymer derived from propylene units and at least one component which is a styrene block copolymer. The polymer compositions exhibit processing properties which are suitable for a multiplicity of applications such as, e.g. films, fibres, fabrics and nonwoven fabrics, plates, mouldings, extruded parts, thermoformed objects, etc. However, no spray applications are described since the systems claimed have melt viscosities which are too high for this application technique.

An important component of disposable absorbent articles is the absorbent core. Typical absorbent cores comprise an absorbent material sandwiched between two layers that form a core wrap. The absorbent material typically includes superabsorbent polymer (SAP) in the form of particles. The SAP ensures that large amounts of bodily fluids, e.g. urine, can be absorbed by the absorbent article during its use and be locked away, thus providing low rewet and good skin dryness.

SAP particles have been conventionally mixed with cellulosic wood fibers. "Airfelt", as used herein, refers to comminuted wood pulp, which is a form of cellulosic fiber. More recently, absorbent cores have been proposed which are free of such cellulosic fibres, and which are made by the so-called SAP printing technology, see for example EP 1,447,067 A1 (Busam et al.), EP 1,621,165 (Blessing et al.). This so called airfelt-free technology enables thinner absorbent cores by the reduction or elimination of the cellulose fibers from the absorbent cores and improved placement of the SAP particles, while maintaining overall absorbency.

The SAP particles should be immobilized in the dry state, that is before usage, and at least to some extent in the wet stage, while the product is in use and has absorbed urine or other exudate. In order to stabilize and maintain the SAP particles in these airfelt-free cores, an immobilizing material in the form of a thin fibrous hotmelt adhesive network that entangles the SAP particles has been used. The molten immobilizing material must be able to be sprayed through a nozzle in the form of microfibers to provide the desired immobilizing network. SAP immobilizing materials in the form of hotmelt adhesive comprised a base polymer along with other materials such as tackifiers, plasticizers, oils, and/or waxes have been used.

For example, WO 2016/149,252 A1 (Stiehl et al.) claims such an immobilizing material having a storage modulus (G') at 21° C. of greater than $1.2 \times 10^6$ Pa. Various thermoplastic polymers are indicated to be suitable including metallocene polyolefins such as ethylene polymers, also styrenic block copolymers such as SIS, SEBS and SBS, and propylene based polymers such as Licocene PP1602 and PP2602.

WO 2017/132,119 (Turner) discloses a superabsorbent immobilizer comprising at least 50% by weight of one or more polymers each having a peak molecular weight of at least 10 kg/mol. Polymers mentioned are selected from the group consisting of polymers and copolymers of propylene, ethylene, butene, and combinations thereof; styrenic block copolymers; polyolefins; olefin block copolymers, and combinations thereof.

WO 2014/194,074 A1 (Remmers et al.) relates to a disposable absorbent article and an adhesive composition including a first polymer that is propylene-based and has a Mw of no greater than about 75,000, and a second polymer selected from a group including propylene based polymers with a Mw of at least about 100,000 and styrene block copolymers with a styrene content of no greater than about 20% where the adhesive composition is useful for elastic attachment applications.

There is a need for an improved immobilizing material that is easily processable, provides the required SAP particles dry and wet immobilization, is chemically stable and has an acceptable odor. The immobilizing material should ideally also be usable to bond other layers in the absorbent article, such as for nonwoven-nonwoven bonds or nonwoven-film bonds.

SUMMARY OF THE INVENTION

The invention is directed to an absorbent article comprising an hotmelt adhesive comprising a styrene-block-copolymer (SBC) blended with an amorphous polyolefin having an enthalpy of fusion of less than 10 J/g and optionally a tackifier. The hotmelt adhesive may for example be applied in the form of a fibrous network that immobilizes the superabsorbent particles on a substrate in the absorbent core. The hotmelt adhesive is advantageously also suitable for adhesive bonding of other components of the absorbent article.

The inventors have found that SBC polymers, which are highly viscous and as such unconvertible, can be made processable by blending with an amorphous polyolefin. The presence of crystalline or semi-crystalline polyolefins is preferably limited or completely avoided in the formulation. The amorphous polyolefin may be in particular a propylene-based copolymer having a weight-average molecular weight $M_w$ of less than 10 000 g/mol.

The SBC polymer may advantageously be a hydrogenated SBC polymer, such as a styrene-ethylene-butadiene-styrene (SEBS), a styrene-ethylene-propylene-styrene (SEPS) and styrene-ethylene-propylene (SEP) polymers.

The hotmelt adhesive may also contain other ingredients such as tackifiers, plasticizers, organic or inorganic pigments, fillers, stabilizers, antistatics, antioxidants and light stabilizers. If present, tackifiers which are hydrogenated are preferred. By using hydrogenated components, the immobilizing material is less odorant and more stable than related component having double bonds. Hydrogenated tackifier can optionally help the blending of the adhesive components. The hotmelt adhesive can be and is preferably formulated with low amount or even be free of mineral oil.

BRIEF DESCRIPTION OF THE DRAWINGS

The above-mentioned and other features and advantages of the present disclosure, and the manner of attaining them, will become more apparent and the disclosure itself will be better understood by reference to the following description of example forms of the disclosure taken in conjunction with the accompanying drawings, wherein:

FIG. 5 shows a longitudinal cross-section view of the absorbent core of FIG. 4;

FIG. 6 shows transversal cross-section view of the absorbent core of FIG. 4;

DETAILED DESCRIPTION

Definitions

"Absorbent article" or "personal hygiene absorbent article", as used herein, refers to products that are placed against or in proximity to the body of a wearer to absorb and contain the various exudates discharged from the body. As used herein, the term "body fluids" or "body exudates" includes, but is not limited to, urine, blood, vaginal discharges and fecal matter. Absorbent articles include in particular taped or pant baby diapers, training pants, adult incontinence undergarments, feminine hygiene products, and the like.

"Amorphous" refers herein to the substantial absence of crystallinity, in particular to polymers having an enthalpy of fusion of less than 10 J/g, as measured according to ISO 11357-2 (2013). The enthalpy of fusion can preferably be less than 5 J/g, or less than 1 J/g and down to 0 J/g. The amorphous nature of the polyolefin material results in a melting point, which is not sharp or definite. Rather as the temperature increases, amorphous polymers gradually change from a solid to a soft and then to a liquid material.

"Comprise," "comprising," and "comprises", as used herein, are open ended terms, each specifies the presence of what follows, e.g., a component, but does not preclude the presence of other features, e.g., elements, steps, components known in the art, or disclosed herein.

"Consisting essentially of", as used herein, limits the scope of subject matter, such as that in a claim, to the specified materials or steps and those that do not materially affect the basic and novel characteristics of the subject matter. The term "Consisting of" further limits the scope to the specified elements, steps, or components.

"Diaper", as used herein, refers to an absorbent article generally worn by infants and incontinent persons about the lower torso so as to encircle the waist and legs of the wearer and that is specifically adapted to receive and contain urinary and fecal waste. As used herein, term "diaper" includes taped diapers and pant diapers, which is defined below.

"Pants" refer to disposable articles having a waist opening and leg openings designed for infant or adult wearers. A pant may be placed in position on the wearer by inserting the wearer's legs into the leg openings and pulling the pant into position about a wearer's lower torso. A pant may be preformed by any suitable technique including, but not limited to, joining together portions of the article using refastenable and/or non-refastenable bonds (e.g., seam, weld, adhesive, cohesive bond, fastener, etc.). A pant may be preformed anywhere along the circumference of the article (e.g., side fastened, front waist fastened). While the terms "pant" or "pants" are used herein, pants are also commonly referred to as "closed diapers," "prefastened diapers," "pull-on diapers," "training pants," and "diaper-pants".

Figure 1:
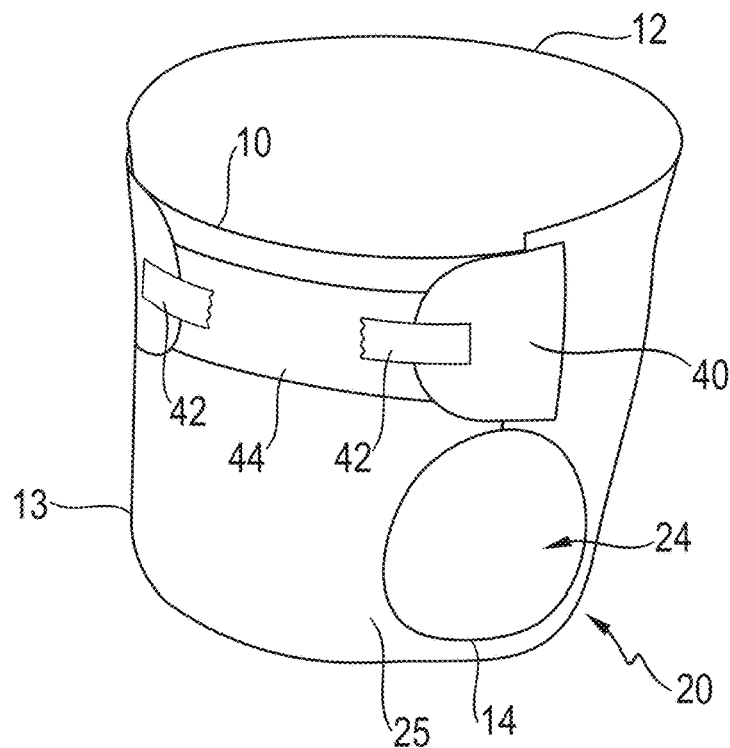
FIG. 1 shows a perspective view of an exemplary taped diaper in a closed configuration as it would be when worn by a wearer.

"Taped diapers" refer to absorbent articles that comprise tapes, typically in the back half of the product, that can be refastenably attached to a landing zone on the front of the diaper to for the waist and leg openings. Such a taped diaper is shown in FIG. 1 for example.

"Fibrous network", as used herein, refers to a hotmelt composition from which strands or a net structure is formed and applied to superabsorbent particles with the intent to at least partially immobilize the superabsorbent polymer particles in both the dry and wet state. The fibrous network may be formed over, around, and/or between the superabsorbent polymer particles.

"Hotmelt adhesives" are thermoplastic compositions solid at room temperature, which when heated are converted into the liquid or molten state, i.e. the hotmelt adhesive is open, and may be applied to a substrate by spraying or by contact applicator. The hotmelt adhesive has an open time optimized for the intended use and effects permanent adhesive bonding of the adherends. The hotmelt adhesive may be applied to superabsorbent particles to immobilize them on a substrate by forming a fibrous network. The hotmelt adhesive may also be used as a construction adhesive to form a bond between two substrates. Hotmelt adhesives may comprise tackifier or be free of tackifier.

"Nonwoven", as used herein, is a manufactured sheet, web, or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than 0.001 mm to greater than 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Substantially", as used herein, means generally the same or uniform but allowing for or having minor fluctuations from a defined property, definition, etc. For example, small measurable or immeasurable fluctuations in a measured property described herein, such as viscosity, melting point, etc. may result from human error or methodology precision. Other fluctuations are caused by inherent variations in the manufacturing process, thermal history of a formulation, and the like. The compositions of the present invention, nonetheless, would be said to be substantially having the property as reported.

General Description of an Absorbent Article

Figure 2:
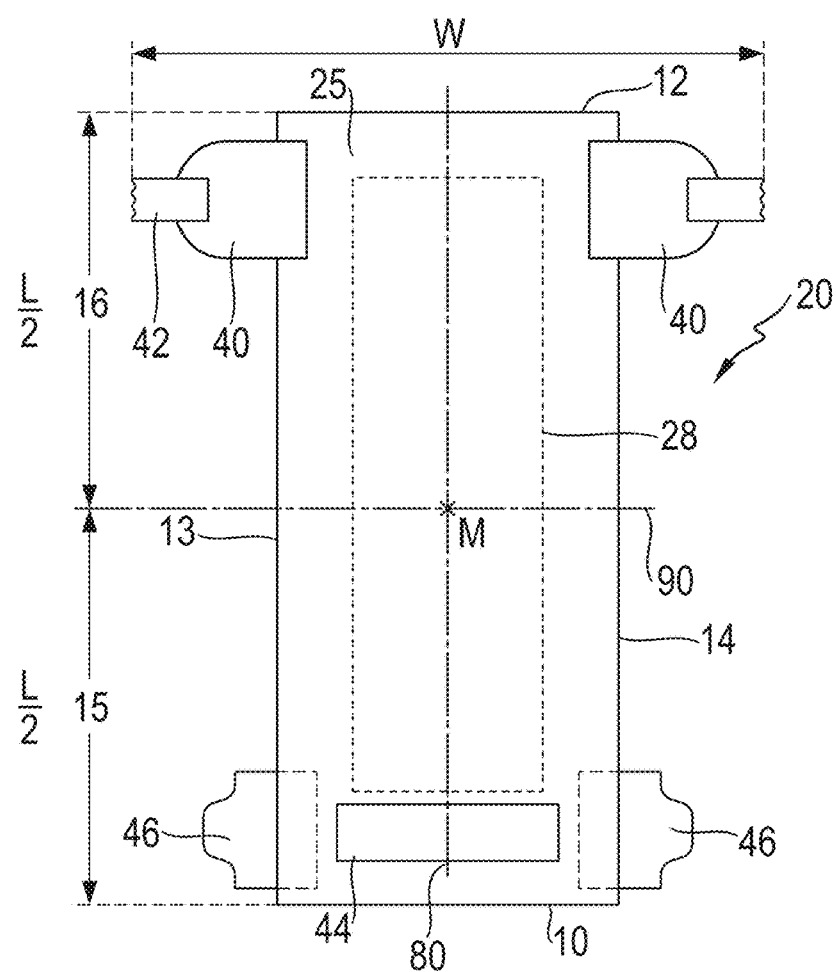
FIG. 2 shows the external-facing side of the diaper of FIG. 1 with the diaper flattened out.
Figure 3:
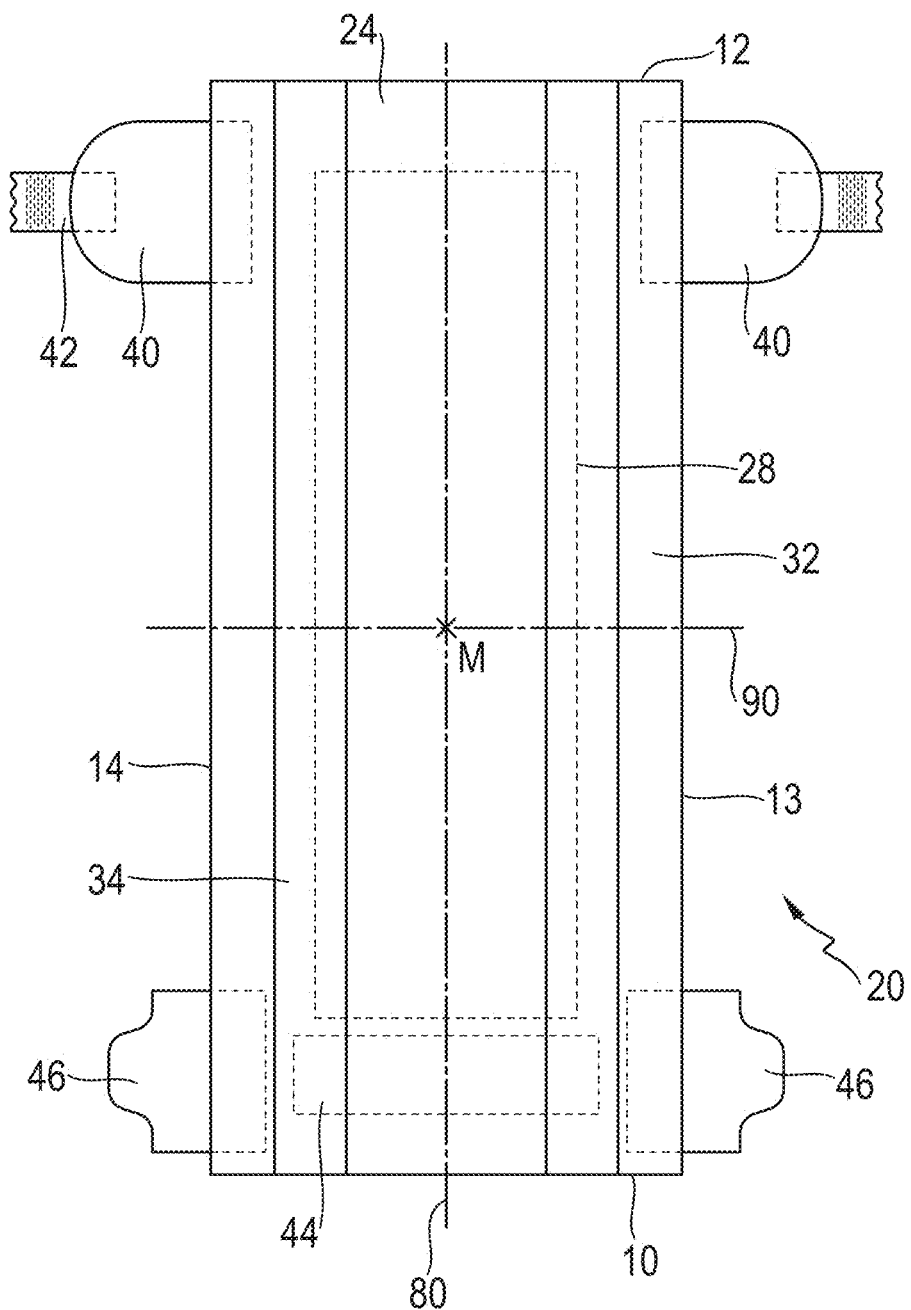
FIG. 3 shows the wearer-facing side of the diaper of FIG. 1 with the diaper flattened out.

An exemplary absorbent article according to the invention in the form of a baby taped diaper 20 is represented in FIGS. 1-3. FIG. 1 is a perspective view of the exemplary diaper in a closed state as it would appear when worn by a wearer. This taped diaper 20 is shown for illustration purpose only as the invention may be used for making a wide variety of diapers or other absorbent articles such as baby diaper pants, adult incontinence pants or feminine sanitary pads. In the following, the word "diaper" and "absorbent article" are used interchangeably. The Figures are used herein as illustration of one way to carry out the invention and are not limiting the scope of the claims, unless specifically indicated to do so.

The absorbent article comprises a liquid permeable topsheet 24 on its wearer-facing surface, a liquid impermeable backsheet 25 on its garment-facing surface and an absorbent core 28 between the topsheet and the backsheet (shown in dotted line in FIGS. 2 and 3). The topsheet typically forms the majority of the wearer-contacting surface of the article and is the first layer that the body exudates contact. The topsheet is liquid permeable, permitting liquids to readily penetrate through its thickness. Any known topsheet may be used in the present invention. The backsheet typically comprises a fluid impermeable plastic film, which may be printed with a backsheet pattern, and a low basis weight nonwoven outer cover glued to this impermeable film to give a nicer feel and appearance to the backsheet.

The absorbent article may also typically comprise a fluid acquisition layer and/or a fluid distribution layer between the topsheet and the absorbent core, which is not represented for simplicity but are present in most diapers, as well as elasticized outer barrier cuffs 32 and elasticized inner barrier cuffs 34, as is known in the art. The absorbent article may also comprise other usual components if it is desired to increase the performance of the article, such as transverse barrier cuffs, front and/or back elastic waistbands, a lotion application on the topsheet, longitudinally extending channels in the core and/or the distribution layer, a wetness indicator, etc., all these components have been extensively described and exemplified in the art. More detailed disclosures of example of such components are for example disclosed in WO 2014/93323, WO 2015/183669 (both Bianchi et al), WO 2015/031225 (Roe et al.) or WO 2016/133712 (Ehrnsperger et al.) to name a few.

The absorbent article typically comprises a front edge 10, a back edge 12, and two longitudinally-extending side (lateral) edges 13, 14. The front edge 10 is the edge of the article which is intended to be placed towards the front of the user when worn, and the back edge 12 is the opposite edge, and together form the waist opening of the diaper. The lateral edges 13, 14 respectively form the two leg openings. The topsheet 24, the backsheet 25, the absorbent core 28 and the other article components may be assembled in a variety of well-known configurations, in particular by gluing, fusion and/or pressure bonding. The absorbent articles of the invention may comprise any typical layers and components used in absorbent products of the diaper type, and which are not necessarily represented in the simplified FIGS. 1-3. A plurality of absorbent articles may be packaged together in a package.

The present invention is also applicable to absorbent articles in the form of pants, in particular pant diapers. Such pant construction comprises a central chassis and a waist belt, as is known in the art. The central chassis comprises a topsheet, backsheet, absorbent core, inner and outer cuffs etc. The components of the chassis including topsheet, backsheet, absorbent core, inner and outer cuffs, can be made of similar components as found in taped diapers. The waist belt comprises a front belt and a back belt, which are elasticized for example by elastic strands, and are sealed at the side edges of the belts to form a ready to use pant shaped disposable absorbent article. A more detailed description of a typical pant construction is for example disclosed in WO2017/173894 (P&G).

Alternatively, instead of attaching belts to the chassis to form a pant, discrete side panels may be attached to side edges of the chassis. Suitable forms of pants comprising discrete side panels are e.g. disclosed e.g. in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744.

General Description of an Absorbent Core

"Absorbent core" means an absorbent structure disposed between topsheet and backsheet for absorbing and containing liquid such as urine received by the absorbent article. The absorbent core comprises an absorbent material, in particular superabsorbent polymer particles, and a core wrap sandwiching the absorbent material. The core wrap may be a single material that is wrapped over the absorbent material or may comprise a separate top layer and bottom layer that are bonded together. The absorbent material may be free of cellulose fibers. The absorbent core may consist essentially of the core wrap, the superabsorbent polymer particles, and an immobilizing material as a fibrous network.

Figure 4:
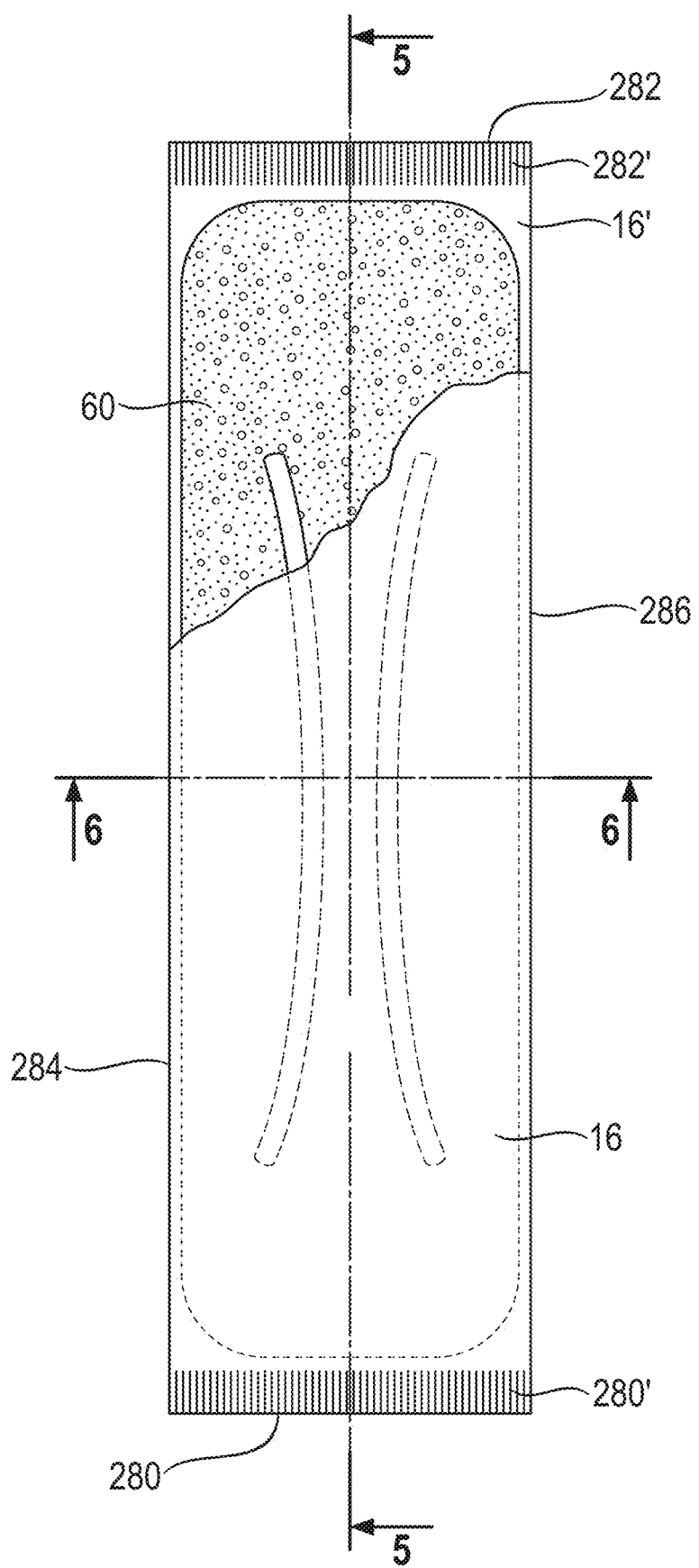
FIG. 4 shows a top view of an exemplary absorbent core with the top layer of the core wrap partially removed.

The absorbent core is typically the component of the absorbent article having the most absorbent capacity. An exemplary absorbent core 28 is shown in isolation in FIGS. 4-6, in dry state (before use). The absorbent core may typically have a generally rectangular shape as defined by the longitudinal edges 284, 286 and transversal front edge 280 and back edge 282. The absorbent core 28 comprises an absorbent material 60, deposited as a layer having a generally rectangular outline, as represented on FIG. 4. This absorbent core represented is of course not limiting the scope of the invention as the invention is applicable to a wide variety of absorbent cores. It is also common to have an absorbent material layer having a non-rectangular outline ("shaped" core), in particular the absorbent material layer may define a tapering along its width towards the central region of the core (or "dog-bone" shape). In this way, the absorbent material deposition area may have a relatively narrow width in an area of the core intended to be placed in the crotch region of the absorbent article. This may provide for example better wearing comfort. Other shapes can also be used such as a "T" or "Y" or "sand-hour" for the area of the absorbent material.

The absorbent material 60 may be any conventional absorbent material known in the art. For example, the absorbent material may comprise a blend of cellulose fibers and superabsorbent particles ("SAP"), typically with the percentage of SAP ranging from 40% to 70% by weight of the absorbent material. The absorbent material may also be free of cellulose fibers, as is known in so-called airfelt-free cores where the absorbent material consists of SAP.

The SAP useful in the present invention includes a variety of water-insoluble, but water-swellable polymers capable of absorbing large quantities of fluids. The term "superabsorbent polymer" refers herein to absorbent materials, which may be cross-linked polymeric materials, that can typically absorb at least 10 times their weight of an aqueous 0.9% saline solution as measured using the Centrifuge Retention Capacity (CRC) test (EDANA method WSP 241.2.R3 (12). The SAP may in particular have a CRC value of more than 20 g/g, or more than 24 g/g, or of from 20 to 50 g/g, or from 20 to 40 g/g, or 24 to 30 g/g. "Superabsorbent polymer particles", as used herein, refers to a superabsorbent polymer material which is in particulate form so as to be flowable in the dry state.

Various absorbent core designs comprising high amount of SAP have been proposed in the past, see for example in U.S. Pat. No. 5,599,335 (Goldman), EP 1,447,066 (Busam), WO 95/11652 (Tanzer), US 2008/0312622 A1 (Hundorf), WO 2012/052172 (Van Malderen). In particular the SAP printing technology as disclosed in US 2006/0024433 (Blessing), US 2008/0312617 and US 2010/0051166 A1 (both to Hundorf et al.) may be used. The invention is however not limited to a particular type of absorbent core. The absorbent core may also comprise one or more glue such as auxiliary glue applied between the internal surface of one (or both) of the core wrap layers and the absorbent material to reduce leakage of SAP outside the core wrap. A micro-fibrous adhesive net may also be used in air-felt free cores as described in the above Hundorf references. These glues are not represented in the Figures for simplicity.

The absorbent material may be deposited as a continuous layer within the core wrap. The absorbent material may also be present discontinuously for example as individual pockets or stripes of absorbent material enclosed within the core wrap and separated from each other by material-free junction areas. A continuous layer of absorbent material, in particular of SAP, may also be obtained by combining two absorbent layers having matching discontinuous absorbent material application pattern wherein the resulting layer is substantially continuously distributed across the absorbent particulate polymer material area. As for example taught in US2008/0312622A1 (Hundorf), each absorbent material layer may thus comprise a pattern having absorbent material land areas and absorbent material-free junction areas, wherein the absorbent material land areas of the first layer correspond substantially to the absorbent material-free junction areas of the second layer and vice versa.

Figure 7:
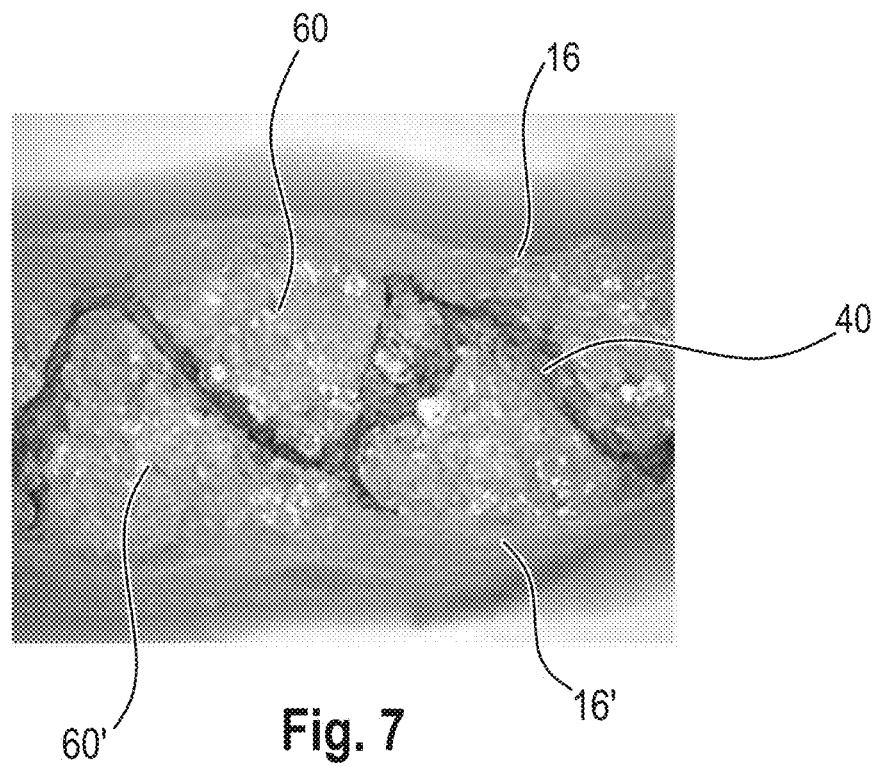
FIG. 7 shows is a magnified picture showing swollen SAP particles immobilized by a fibrous network of an immobilizing material.

FIG. 7 for example shows such a close-up cut picture of an absorbent core, showing a core wrap with a nonwoven top layer 16 and a nonwoven bottom layer 16', two layers of superabsorbent polymer particles 60, 60' (swollen in the picture) each immobilized by a fibrous network of an hotmelt adhesive 40 on their respective substrate. In practice, each layer of SAP particles is immobilized separately by an adhesive fibrous network before the core is formed by merging both absorbent layers together, wherein the two fibrous networks are in contact and no longer distinguishable in the picture.

The basis weight (amount deposited per unit of surface) of the absorbent material may also be varied to create a profiled distribution of absorbent material, in particular in the longitudinal direction (as schematically illustrated in FIG. 5) to provide more absorbency towards the center and the middle of the core, but also in the transversal direction, or both directions of the core. The absorbent core may also comprise longitudinally extending channels 26, which are areas substantially free of absorbent material within the absorbent material area. The core wrap may be bonded through these material-free areas by a core wrap bond 27. Exemplary disclosures of such channels in an airfelt-free core can be found in WO 2012/170778 (Rosati et al.) and US 2012/0312491 (Jackels). Channels may of course also be formed in absorbent cores comprising cellulose fibers. The core wrap bond may be an adhesive bond, in which case the adhesive of the invention may be used, typically as a slot application on the inner surface of one or both of the top layer and bottom layer of the core wrap.

Core Wrap

The function of the core wrap is to enclose the absorbent material. As indicated in the background, different core wrap constructions can be used. Typical core wraps comprise two nonwoven substrates 16, 16', which are attached to another and form respectively the top layer 16 and the bottom layer of the core wrap 16'. These two layers may be typically attached to another along at least part of the periphery of the absorbent core to form a seal. Typically, neither the first nor the second substrate needs to be shaped, so that they can be rectangularly cut for ease of production, but other shapes are not excluded. The terms "seal" and "enclosing" are to be understood in a broad sense. The seal does not need to be continuous along the whole periphery of the core wrap but may be discontinuous along part or the whole of it, such as formed by a series of seal points spaced on a line. Typically, a seal may be formed by gluing and/or thermal bonding.

The core wrap represented in the Figures comprises a top layer 16, which is wider than the bottom layer 16' so that two flaps of the top layer can be folded over the bottom layer along the longitudinal edges 284, 286 of the core respectively to which they are attached, typically by an adhesive, to form the longitudinal seals 284', 286'. The front edge 280 and back edge 282 may also be sealed, for example by a sandwich seal 280', 282'. Such transversal seals may for example made by adhesive stripes applied in machine direction by the slot glue technique, as is known in the art. Alternatively, is it possible to leave the transversal edges 280, 282 open without a seal. For example, there may be enough core wrap material between the edges of the core and the absorbent material 60 to provide a buffer zone at these ends.

The invention is applicable to any of these seals, between the core wrap layers, as well as the core channel bonds 27 that will be discussed further below, as these seals or bonds are typically subject to a peel force once the absorbent material swells for a prolonged length of time. Alternatively, the core wrap may be made of a single piece of nonwoven which has been folded over itself around the absorbent material layer 60, and is bonded to itself along a single longitudinal seal, instead of two longitudinal seals 284' and 286' as represented in the Figures. The invention is also applicable to such a core wrap.

The top layer 16 and the bottom layer 16' may be made from the same base substrate material which has been differently treated. Such nonwoven substrate may have a basis weight within a range of from 8 to 12 gsm. The top layer may be typically a nonwoven layer made of synthetic fibers that has been treated with a surfactant to increase its hydrophilicity. Both layers may in particular each comprises or consists of a nonwoven web, such as a carded nonwoven, a spunbond nonwoven ("S") or a meltblown nonwoven ("M"), and a multi-layer of any of these. For example, spunbond/meltblown laminate (spunmelt) polypropylene nonwovens are commonly used and are particularly suitable, especially those having a multi-layer SMS, or SMMS, or SSMMS, structure. Examples are disclosed in U.S. Pat. No. 7,744,576, US 2011/0268932 A1, US 2011/0319848 A1 or US 2011/0250413 A1. Typical material used to make the synthetic fibers are PE (polyethylene), PET (polyethylene terephthalate) and in particular PP (polypropylene).

Spunbond, also called spunlaid, nonwovens are made in one continuous process. Fibers are spun through a number of small orifices in a spinneret to form fibers or filaments, which are then directly dispersed into a web by deflectors or can be directed with air streams on a moving foraminous surface, such as a wire mesh conveyor. Meltblown nonwovens are produced by extruding melted polymer fibers through a spinneret or die consisting of up to 40 holes per inch to form long thin fibers which are stretched and cooled by passing hot air over the fibers as they fall from the die. The diameters of the fiber are significantly reduced by hot air which also breaks the continuous filaments into microfibers of varying length to diameter ratio. The extremely fine fibers (typically polypropylene) differ from other extrusions, particularly spunbond, in that they have low intrinsic strength but much smaller size offering key properties.

The spunbond process can be combined with the meltblown process to form a multi-layer web having S (spunbond) layer and M (meltblown) layer, in particular SM, SMS or SMMS webs, which are strong and offer the intrinsic benefits of fine fibers. The nonwovens may be consolidated using known techniques, typically thermal point bonding. In thermal point bonding, heat is applied locally on individual regions of the nonwoven to locally melt and fuse the fibers together. Fusion bond patterns are for example disclosed in US 2011/0250413 (Hu et al.) and US 2014/0072767 A1 (Klaska et al.). The resultant web is typically collected into rolls at the supplier and subsequently converted to finished products.

Core Channels

The absorbent core 28 may comprise one or more channels, in particular at least two channels 26, within the absorbent material layer. The channels may in particular be areas substantially free of absorbent material, in particular areas completely free of absorbent material (accidental minute amount of absorbent material due to involuntary contamination of the channels due to the high speed of the making process being disregarded).

The channels 26 may comprise a bond 27 between the top side 16 of the core wrap and the bottom side 16' of the core wrap. This bond 27 provides for structural integrity of the channels in dry and wet state. Any known bonding techniques known in the art may be used to provide for this bond, in particular one selected from adhesive bonding, thermo bonding, mechanical bonding, ultrasonic bonding, or any combinations thereof. An adhesive may be for example applied in the areas of the channels on the inner side of the top side and/or the inner side of the bottom side of the core wrap, typically by slot glue application or any other means, followed by the application of pressure in the areas of the channels to provide a good adhesive bonding in these areas. Exemplary patent disclosures of such adhesive bonding processes can be found for an airfelt or airfelt-free absorbent cores in WO 2012/170798 A1 (Jackels et al.), EP 2,905,000 (Jackels et al.) and EP 2,905,001 (Armstrong-Ostle et al.).

The adhesive of the invention may be used to make these channel bonds 27, in addition or alternatively to the core perimeter bonds 280'-286'. Typically, the bonds 27 may generally have the same outline and shape as the channel areas 26 in which they are contained, but may be slightly smaller to allow for a safety margin (e.g. by a few mm) as some deviations from the optimal registration may happen during high speed process. It is expected that channel bonds 27 may be more efficiently made and stronger if they are provided in macroscopic areas with no absorbent material (except of course accidental contamination) compared to bonds provided in areas containing non-negligible absorbent material.

Backsheet

The backsheet 25 is the liquid impermeable layer that generally form the garment-facing side of the absorbent article. The backsheet 25 prevents, or at least inhibits, the bodily exudates absorbed and contained in the absorbent core 10 from soiling articles such as bedsheets, undergarments, and/or clothing. The backsheet typically comprises a liquid impermeable, or at least substantially liquid impermeable layer, such as a thin plastic film having a thickness of about 0.012 mm to about 0.051 mm. Suitable backsheet materials also include breathable materials which permit vapors to escape from the absorbent article, while still preventing, or at least inhibiting, bodily exudates from passing through the backsheet.

The backsheet 25 typically further comprises on its external side a nonwoven outer cover for improving the overall feel of the backsheet. The outer cover material (sometimes referred to as a backsheet nonwoven) is typically a nonwoven material joined to and covering the backsheet film. Thus the outer cover material typically forms at least a portion of the garment-facing surface of the absorbent article 20. The outer cover material may comprise a bond pattern, apertures, and/or three-dimensional features.

Landing Zone

Referring to FIGS. 1 and 2, the absorbent article 20 in the form of a taped diaper may have a discrete landing zone 44 on its garment-facing side, typically disposed proximate the front edge 10 of the article 20. The landing zone 44 is configured to receive the fasteners 42 and may comprise, for example, a plurality of loops configured to be engaged with, a plurality of hooks on the fasteners 46, or vice versa.

The landing zone 44 typically comprises one or more discrete nonwoven materials that are attached to a portion of the outer cover material 40 in the front waist region 12. The present invention is in particular applicable to the bond area between such a landing zone 44 and the backsheet outer cover 25.

Hotmelt Adhesives

The hotmelt adhesives of the invention comprise a styrene-block-copolymer (SBC), an amorphous polyolefin and optionally a tackifier. Each of these components are disclosed below in more details. The SBC is preferably also amorphous. If present, the tackifier is preferably hydrogenated. Conventional additives such as UV stabilizer, antioxidant, antistatics, odor reducing agents, may also be incorporated in the immobilizing material as is known in the art, typically in low amount (each <2 w. %).

The hotmelt adhesives may be particularly useful as SAP immobilizing material that is applied to the superabsorbent polymer particles to at least partially immobilize the superabsorbent polymer particles in the dry and wet state. The hotmelt adhesive used as immobilizing material is typically heated at a sufficiently high temperature to become liquid and is then sprayed on the superabsorbent particles. As the sprayed immobilizing material cools, it forms a solid fiberized network with microfibers or nanofibers that interweaves or intertwines with the particles of superabsorbent polymer. An exemplary process for making an airfelt-free absorbent core and spraying the immobilizing material is disclosed in the reference indicated in the background section, such as EP 1,447,067 A1 (Busam et al.). As disclosed therein, a layer of SAP particles may be first disposed (e.g. SAP printing technology) on a substrate such as nonwoven layer, optionally with an auxiliary adhesive between the substrate and the SAP layer, and the immobilizing material homogeneously sprayed thereon to form the immobilizing fibrous network. A second substrate may then be applied on the immobilized layer to form a core wrap. The absorbent core may comprise two such layers of immobilized superabsorbent particles, as disclosed in the cited references.

The hotmelt adhesives of the invention may also be used as construction adhesive to bond any two components in the absorbent article, in particular to make any types of nonwoven to nonwoven bonds, film to nonwoven bonds, and elastic strands to film or nonwoven bonds.

The hotmelt adhesives used in the invention have a well-balanced ratio of mechanical properties and may be applied by energy-efficient and material-efficient application techniques, while nevertheless ensuring high mechanical stability and flexibility of the adhesive bond and thus opening up possible uses that place increased demands on the stability of the adhesive bond. Mention may be made here in particular of adhesive fibers web spray applications which affix SAP powders without impairing mass transfer with the environment and which can also stabilize expanding and contracting systems by liquid absorption.

Advantageously, the hotmelt adhesive is substantially free of mineral oils, what means in the sense of this invention that the mineral oil content in the thermoplastic material is below 1%, in particular below 0.1%, by weight. The hotmelt material may comprise organic or inorganic pigments, fillers, stabilizers, antistatics, antioxidants and light stabilizers. The hotmelt may be completely free of mineral oils.

The hotmelt material may comprise a tackifier which positively influences the adhesion to the substrate, or alternatively be free of tackifier. When present, the tackifier is preferably hydrogenated.

Styrene-Block-Copolymer (SBC)

The hotmelt adhesive of the invention typically comprises at least about 10% by weight of the composition of one or more styrene-block-copolymer(s) (SBC). The SBC may be a single material of a mixture of SBC copolymers. "SBC" is thus used herein to mean one styrene-block-copolymer or a mixture of styrene-block-copolymers. The hotmelt adhesive may typically comprise from about 10% to 60%, or from about 15% to about 50%, or from about 20% to about 45%, by weight of the hotmelt adhesive, of SBC. The SBC content may be higher if the hotmelt is free of tackifiers. The SBC may typically have a styrene content of 10% to 40%, preferably from 10% to 20%, particularly preferably of from 20% to 35%, by weight, based on the total mass of the SBC.

The SBC may typically be an elastomeric triblock copolymer of the A-B-A type, wherein A consists of rigid styrene units and B of elastomeric units. The B blocks may in particular be partly hydrogenated conjugated diene. The B block may be selected from the group consisting of poly(ethylene-butylene) (hydrogenated polybutadiene) to form a SEBS copolymer, or poly(ethylene-propylene) (hydrogenated polyisoprene) to form a SEPS copolymer, and mixtures thereof. A nonlimiting example of a commercially available SEBS co-polymer is Kraton MD 1648, which has a glass transition temperature of −50° C., as measured using the Glass Transition Temperature Test Method described herein, and a fusion index of 0%, as measured using the Fusion Index Test Method described herein.

In addition to the elastomeric triblock copolymer of the ABA type, the SBC may also comprise an elastomeric diblock copolymer of the AB type (in particular SEP diblock copolymer) or an elastomeric (A-B)n multiblock copolymer, where n is the number of blocks.

The SBC may be preferably selectively hydrogenated at the double bonds in the polymer chain, what is characterized by an Iodine number below 100 g $I_2$ per 100 g of polymer, particularly preferably below 50 g $I_2$ per 100 g of polymer.

The SBC can also be a hydrogenated styrene block copolymer with high vinyl content, low viscosity, and low order-disorder temperature as described in US 2019/0292361 (Flood et al., assigned to Kraton Polymers LLC).

The SBC may have weight-average molecular weight (as measured according to DIN 55672) of more than 30,000 g/mol, or more than 40,000 g/mol, or more than 50,000 g/mol, in particular from 50,000 to 300,000 g/mol, or from 70,000 to 150,000 g/mol.

The SBC may have a melt flow rate MFR (230° C./2.16 kg) of less than 250 g/10 min, determined in accordance with ASTM 1238.

The SBC may have a fusion index from about 0% to about 15%, as measured using the Fusion Index Test Method described herein, and a glass transition temperature of below 0° C., as measured using the Glass Transition Temperature Test Method described herein.

The SBC may be a hydrogenated styrene block copolymer with high vinyl content, low viscosity, and low order-disorder temperature as described in US 2019/0292361 (Kraton).

Hydrogenated SBC polymers such as SEBS or SEPS are highly viscous, and as such they are difficult to spray to form a fibrous network on the superabsorbent particles without further measures. The inventors have now found that it is possible to blend these SBC polymers with amorphous polyolefins as disclosed below to increase their processability.

The inventors have also found that a hydrogenated tackifier may further serve as compatibilizer for both components instead of mineral oil.

Amorphous Polyolefins

The present inventors have found that blending the SBC with an amorphous polyolefin provides an adhesive which is processable and has the required properties to immobilize SAP particles in dry and wet form. The hotmelt composition may comprise a single amorphous polyolefin or a mixture thereof. In the following, "amorphous polyolefin" means "at least one amorphous polyolefin(s)", unless specified otherwise. The hotmelt adhesive comprises at least 10% by weight of such amorphous polyolefin, in particular the amorphous polyolefin content may range from 10% to 60%, in particular from 20% to 50%, or from 25% to 40%, by weight of the hotmelt adhesive. Higher amounts are possible, especially if the hotmelt is free of tackifiers.

While not wishing to be bound by theory, it is believed that the presence of semi-crystalline (heterophase) polyolefins in hotmelt formulations of the prior art may cause a loss of strengths of the fibrous network when stretched by the swelling of the SAP particles. It is conjectured that upon stretching, the crystal domains of a semi-crystalline polyolefin may irreversibly break and dissipate the mechanical energy of mechanical deformation into heat. This makes semi-crystalline polyolefins visco-plastic. The net loses its strengths upon stretching and over time in the stretched state and behaves like a "worn out rubber", in an analogy. SBCs are in contrast to a high extent hyper-elastic. Upon stretching of the adhesive fibers, the mechanical energy is to a substantial extent stored in the stretched adhesive fibers, which prevents a weakening of the stretched fiber via plastic flow or creep over time. The stretched fiber is able to keep its elastic retaining force which makes the whole fiber net more stable against mechanical impact. Thus, after the SAP has swollen and the fibers have been extended, the fibrous network continues to keep its mechanical strength. Such fibers will better withstand the mechanical impact when a baby wearing a loaded diaper rapidly sits down or falls onto the buttock.

The amorphous polyolefin preferably has an enthalpy of fusion, measured in accordance with ISO 11357-2, of less than 10 J/g, preferably of less than 5 J/g, more preferably less than 1 J/g. The amorphous polyolefin preferably has no crystallinity and thus has an enthalpy of fusion of (about) 0 J/g.

The amorphous polyolefins may be characterized by any or all of the following properties:
  a pour point of <50° C., preferably <30° C., more preferably <25° C.;

a viscosity at 170° C. between 20 and 3000 mPa·s, preferably from 50 to 1000 mPa·s, particularly preferably from 80 to 500 mPa·s (measured according to DIN 53019);

a density at 23° C. of less than 0.95 g/cm³, preferably of less than 0.92 g/cm³, in particular between 0.83 g/cm³ and 0.90 g/cm³ (as measured according to ISO 1183);

a glass transition temperature of <−35° C., preferably <−40° C., more preferably<−45° C., as determined by the DSC method according to DIN 11357-2;

a polydispersity index of less than 5, preferably less than 3, particularly preferably less than 2.5. The polydispersity index PDI is calculated from the quotient of weight-average molecular weight Mw and number-average molecular weight Mn and was determined according to the standard ISO 16014.

The amorphous polyolefin has advantageously a weight average molecular weight measured according to DIN 55672 between 1,000 and 50,000 g/mol, preferably between 5,000 and 30,000 g/mol. In particular, the amorphous polyolefin used may be a propylene-based copolymer having a weight-average molecular weight Mw of less than 10,000 g/mol, and which was produced by metallocene catalysis, such as Licocene PPA 330 from Clariant. The amorphous polyolefin exemplified herein is a propylene-based copolymer having a weight-average molecular weight $M_w$ of less than 10,000 g/mol, however it is believed that other amorphous polyolefins are also suitable.

The amorphous polyolefin such as the propylene-based polymers of the invention can both support the function of the base polymer and replace the functions of the plasticizer and the tackifier in the formulation. This results in further advantages for the user. For example, fewer components need to be melted and mixed, thus resulting in faster and more cost-effective working processes.

The amorphous polyolefin of the invention preferably comprises or consists of at least one propylene-based polymer (herein "PbP"). PbP means in the context of this invention linear propylene homopolymers or copolymers produced using Ziegler or metallocene catalysts which have a propylene content of at least 50% by weight or more. The PbP may advantageously be low molecular weight polymer.

The term PbPs covers both propylene-based polymers which were not grafted (PbP-ng) and propylene-based polymers which were grafted with (i) vinyl aromatic monomers (PbP-g-VAM) including PbPs grafted with styrene (PbP-g-ST) or (ii) PbPs grafted with unsaturated vinyl monomers including a heteroatom (PbP-g-UVMH), such as PbPs grafted with maleic anhydride (PbP-g-MAs). The term PbP-g-VAM as used in this application corresponds/is identical to the term PbP-g-St as defined in U.S. Provisional 62/966,140 which priority is claimed.

If this application refers only to PbPs which are not grafted, these are indicated as non-grafted PbPs (PbP-ng). PbP-backbone means in the context of this invention the linear PbP, produced using Ziegler or metallocene catalysts, without substitution at the grafting sites.

The PbP-ngs used in the hotmelt adhesive according to the invention are described, for example, in WO 2018/073, 088, where they are a constituent of non-sprayable permanently tacky pressure-sensitive adhesives.

The use of PbPs in the hotmelt adhesive according to the invention ensures a better integration thereof into the SBC matrix, thus resulting in reduced migration ("bleedthrough") and reduced formation of volatile organic compounds ("VOCs").

The propylene-based polymers may be grafted with 1 to 50% by weight, preferably with 3 to 30% by weight and particularly preferably with 5 to 20% by weight, based on the total weight of PbP-backbone, of vinyl-aromatic monomers (PbP-g-VAM), preferably styrene and its derivatives (PbP-g-ST).

Alternatively, the one or more propylene-based polymers (PbP-ngs) may be grafted with 0.1-20% by weight, preferably with 0.5 to 15% by weight, particularly preferably with 1 to 10% by weight, based on the total weight of PbP-backbone, of unsaturated vinyl monomers including a heteroatom (PbP-g-UVMH), preferably of carboxylic anhydrides, particularly preferably of maleic anhydride (PbP-g-MA).

The PbP-g-VAM or PbP-g-UVMH are manufactured by performing a graft reaction on a PbP-ng as described according to the following method:

Suitable starting materials for the production of the PbP-g-VAM or PbP-g-UVMH are PbP-ngs (low molecular propylene homopolymers or copolymers produced using Ziegler or metallocene catalysts having a weight-average molecular weight $M_w$ of less than 10 000 g/mol). Preferred PbP-ngs have a melt viscosity at 170° C. between 20 and 1000 mPa·s, such as PbPs. Particularly preferred starting materials are low molecular propylene homopolymers or copolymers characterized by a low crystallinity and a statistic distribution of the comonomers and a predominantly to completely atactic structure of the polypropylene parts. The degree of crystallinity of propylene homopolymers or copolymers can be varied in a wide range in a known manner by appropriate selection of the catalyst and the polymerization conditions. This applies in particular when using metallocene catalyst systems.

Suitable materials preferably comprise propylene and one or more other monomers selected from the group consisting of ethylene and higher α-olefins of $C_4$-$C_{18}$. The starting materials particularly preferably comprise propylene and ethylene.

Vinyl-aromatic monomers (VAM) such as styrene, or styrene derivatives that are substituted in the ring and have linear or branched alkyl substituents such as C.-methylstyrene, p-tert-butylmethylstyrene, 1,3-dimethylstyrene, or alkoxylated styrene derivatives are suitable as grafting components, preferably styrene and its derivatives, particularly preferably styrene. The grafting component is used in an amount of 0.1 to 50% by weight of the starting material.

Unsaturated vinyl monomers including a heteroatom (UVMH), preferably carboxylic anhydrides, particularly preferably maleic anhydride (MA) are suitable as grafting components. The UVMH-component is used in an amount of 0.1 to 20% by weight of the starting material.

Suitable radical initiators are components which sufficiently decay into radicals under reaction conditions, such as organic peroxides, for instance alkyl-, aryl- or acyl-peroxides such as di-tert.-butyl peroxide, dibenzoyl peroxide or dicumyl peroxide, peroxyesters such as tert-butyl peracetat or tert.-butyl perbenzoat and hydroperoxides such as tert.-butylhydro peroxid or cumol hydroperoxide. Further possible radical initiators are aliphatic azo compounds such as azo-bis-(2-methyl propionitril) or 2,2'-azo-bis-(2,4-dimethyl valeronitril). Dialkyl peroxide is preferred. Di-tert.-butylperoxid is particularly preferred. The radical initiator is used in an amount of 0.1 to 50% by weight of the PbP.

The reaction of the PbP with the grafting component can take place continuously as well as discontinuously. With the discontinuous process the propylene-based material is heated to a temperature above the melting temperature of the wax, preferably between 100 C and 200° C., particularly preferably between 130° C. and 180° C., and the grafting component as well as the radical initiator are added continuously for an adequate period while agitating or in one or more portions and if applicable under an inert gas atmosphere. After finished dosage, optionally after addition of an additional amount of radical initiator, a post reaction at the same or a different temperature may follow. Volatile components which were generated during the reaction or superfluous volatile starting materials may be distilled under vacuum and/or be separated by stripping with inert gas.

Such modified propylene-based polymers grafted with vinyl-aromatic monomers such as styrene, or styrene derivatives that are substituted in the ring and have linear or branched alkyl substituents such as C.-methylstyrene, p-tert-butylmethylstyrene, 1,3-dimethylstyrene, or alkoxylated styrene derivatives have a wide range of possible applications as compatibilizer or adhesive base polymer, for special applications such as the application in the use in hot melt adhesives, especially in combination with SBCs and/or PbP-ngs.

The PbP-g-VAMs may advantageously be characterized by a PbP-backbone with a weight-average molecular weight of less than 10,000 g/mol, preferably less than 9,000 g/mol, particularly preferably less than 7,000 g/mol, a styrene content between 1 and 50% by weight, preferably, between 2 and 40% by weight, particularly preferably between 5 and 30% by weight and a melting enthalpy below 50 J/g, preferably below 30 J/g, more preferably from 0 to 5 J/g and particularly preferably of 0 J/g.

The PbP-g-UVMHs may advantageously be characterized by a PbP-backbone with a weight-average molecular weight of less than 10,000 g/mol, preferably less than 9,000 g/mol, particularly preferably less than 7,000 g/mol, a carboxylic anhydride content between 0.1 and 20% by weight, preferably between 0.5 and 15% by weight, particularly preferably between 1 and 10% by weight, and a melting enthalpy below 50 J/g, preferably below 30 J/g, more preferably between 0 and 5 J/g and particularly preferably of 0 J/g.

The PbP-g-VAM or PbP-g-UVMH may be characterized by a weight-average molecular weight of less than 20,000 g/mol, preferably less than 15 000 g/mol, particularly preferably less than 10,000 g/mol The hotmelt adhesive may comprise a styrene block copolymer (SBC) and one or more PbPs selected from the group consisting of PbP-ngs having a weight-average molecular weight Mw of less than 10,000 g/mol, PbP-g-VAMs having a weight-average molecular weight of less than 20,000 g/mol and PbP-g-UVMHs having a weight-average molecular weight of less than 20,000 g/mol, wherein the SBC comprises a styrene content of 10 to 40% by weight.

Advantageously the sprayability and the improved mechanical properties of the hotmelt adhesive are achieved by PbPs, which comprise at least one PbP-ng having a pour point, determined according to ASTM D97, below 50° C., preferably below 30° C. and more preferably below 25° C. or at least one PbP-g-VAM or PbP-g-UVMH having a pour point, determined according to ASTM D97, below 85° C. preferably below 60° C., more preferably below 55° C.

Advantageously the PbPs have a melt viscosity at 170° C., measured in accordance with DIN 53019, of 1-1000 mPas, preferably of 1-500 mPas, particularly preferably of 1-300 mPas, which further contributes to the sprayability of the thermoplastic moulding material.

Advantageously the thermoplastic moulding material comprises both one or more PbP-ng and (i) one or more PbP-g-VAM, preferably one or more PbP-g-ST or (ii) one or more PbP-g-UVMH, preferably one or more PbP-g-MA in varying proportions by weight. Such an embodiment facilitates a better miscibility of the polymer components and therefore improved mechanical properties. Surprisingly the combination of PbP-ng and PbP-g-VAM or PbP-g-UVMH enables a lower viscosity of the thermoplastic moulding material in comparison to the thermoplastic moulding material solely comprising PbP-ng although the PbP-g-VAM, preferably PbP-g-ST or PbP-g-UVMH, preferably PbP-g-MA itself has a higher viscosity than the PbP-ng. Another technical feature of this embodiment is a reduced migration of the components.

The PbP-g-VAM or PbP-UVMH polymer can have the same or a different polymer backbone as the PbP-ng. Preferably the PbP-backbone of the PbP-g-VAM or PbP-UVMH polymer is the same as of the PbP-ng. In a preferred embodiment, the hotmelt adhesive comprises SBCs and PbPs, which can be PbP-ng and/or PbP-g-VAM or PbP-UVMH derived from the same or another PbP-backbone. Preferably the PbP-g-VAM or PbP-UVMH is derived from the same PbP-backbone as the PbP-ng.

Advantageously the PbP-backbone is produced by metallocene catalysis. In a further preferred embodiment, the PbP is a copolymer of propylene and another monomer selected from the group consisting of ethylene and $C_4$-$C_{18}$ α-Olefins.

The hotmelt adhesive according to the invention may comprise further polyolefin-based copolymers in addition to the PbPs having a $M_w$ of less than 10,000 g/mol.

In a further preferred embodiment, the PbPs have a glass transition temperature $T_g$, determined by DSC in accordance with DIN EN ISO 11357-2, of less than −20° C., preferably less than −30° C. and particularly preferably less than −40° C.

The PbPs are preferably random copolymers of propylene with a propylene proportion of less than 90% by weight, preferably with a propylene proportion between 60-85% by weight.

The PbPs preferably are copolymers of propylene and ethylene, wherein said copolymer is derived from 60-85% by weight propylene and from 15-40% by weight ethylene.

The use of propylene-based polymers in the hotmelt adhesive of the invention ensures a better integration thereof into the SBC matrix, thus reducing or avoiding migration of the propylene-based polymers out of the SBC matrix (diffusing into adjacent materials). As the hotmelts of the invention preferably have no or reduced amount of mineral oil, there is no possibility of migration of oil and reduced formation of volatile organic compounds ("VOCs"). The hotmelt material may further comprise a styrene grafted propylene-based polymer to improve the integration of the polyolefin-based material into the SBC matrix and therefore to reduce the migration of the polyolefin component. The styrene grafted propylene-based polymer can have the same or a different polymer backbone and/or tacticity as the propylene-based polymer. Preferably the polymer backbone and/or the tacticity of the styrene grafted propylene-based polymer is the same as of the propylene-based polymer.

Properties of the Hotmelt Adhesive

Figure 8:
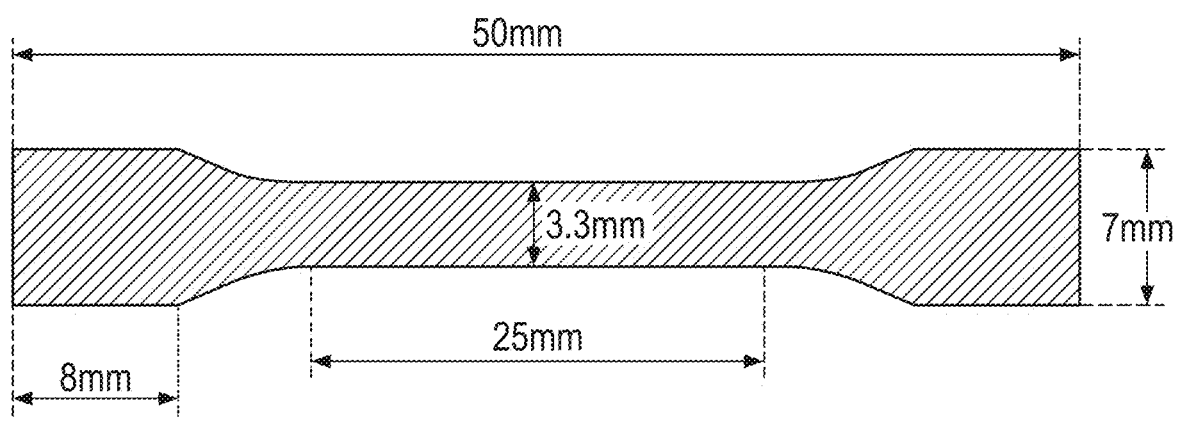
FIG. 8 shows the dumbbell-shaped test specimen used for measuring certain mechanical properties of hotmelt material.

The hotmelt adhesive according to the invention advantageously has one or more or all of the following properties:
  a melt viscosity, measured in accordance with DIN 53019 at 170° C., of between 100-30,000 mPas, preferably between 500-20,000 mPas, particularly preferably between 1,000-15,000 mPas. An optimal spraying result is achievable with the spraying methods suitable for the application in these viscosity ranges;

a tensile strength of at least 2 MPa, measured in accordance with ISO 527, with the exception that the dumbbell-shaped test specimen used (cf. FIG. 8) has the following dimensions deviating from the specification according to ISO 527: total length: 50 mm, width of narrow part: 3.3 mm, width at ends: 7 mm, length of narrow parallel part: 25 mm, thickness: 1 mm. The tensile strength is determined according to ISO 527 by a tensile elongation test. This determines the force per unit area (reported in MPa) required to elongate the test specimen;

an elongation at break of more than 800%, preferably of more than 1,000%, measured in accordance with ISO 527, with the same modified test specimen (cf. FIG. 8). Elongation at break is a measure of the deformation behavior of a polymer and is determined according to ISO 527 by a tensile elongation test in the same test run as for determination of strength. The value for elongation at break indicates the percentage elongation of the test specimen until failure of the material:

a resilience of more than 70%, preferably of more 80%, more preferably of more than 90%, wherein the resilience is determined by the method described in the experimental section (the resilience is a measure of the restoration force of the thermoplastic moulding material);

a Strain Hardening Index higher than 25, optionally up to 1,000, as measured according to the Extensional Test Method;

a Storage Modulus at 100° C. of more than 200 Pa, optionally up to 100,000 Pa, as measured by the Oscillatory Rheometry Test Method;

a Storage Modulus at 25° C. of less than $1.2 \times 10^9$ Pa, as measured by the Oscillatory Rheometry Test Method, optionally from $0.2 \times 10^9$ to $1.2 \times 10^9$ Pa;

a tan δ@100° C. or less than 10, preferably less than 5, as measured by the Oscillatory Rheometry Test Method.

Tackifiers—Other Ingredients

Tackifiers are typically odorous materials which may give a characteristic smell to an absorbent article. To improve the consumer perception of the product, it has been suggested to avoid such smell by avoiding the use of tackifiers altogether (tackifier-free compositions). However, it has been found difficult to formulate an immobilizing material with the required properties without any tackifier, namely which does not phase separate and become inhomogeneous. While the use of tackifier may be low or eliminated in the present invention, it is believed that an hydrogenated tackifier can help homogenize the blend of (preferably hydrogenated) SBC and the amorphous polyolefin, while at the same time providing adhesion at an acceptable moderate level. It is believed in particular that tackifiers comprising a cyclic ring are especially compatible with the polystyrene block of the SBC polymer.

A particular example of tackifier is a hydrogenated C5/cyclic/aromatic hydrocarbon tackifier resin. Such resin if for example commercially available as SUKOREZ SU400 from Kolon. SUKOREZ SU400 is a water-white adhesive tackifier resin based on hydrogenated C5/cyclic/aromatic hydrocarbon resin.

In addition to the styrene-block-copolymer (SBC), the amorphous polyolefin and the optional tackifier discussed above, the hotmelt adhesive may contain usual additional ingredients such as plasticizers, organic or inorganic pigments, fillers, stabilizers, antistatics, antioxidants and light stabilizers. A possible antioxidant is a hindered amine light stabilizer (HALS), which inhibits the emerging odor of the hotmelt material.

The hotmelt adhesive can be advantageously formulated with low amount or even be free of mineral oil, which can cause an undesirable odor. The hotmelt material according to the invention may be also free of plasticizers.

In the context of the invention tackifier- and mineral oil-free is to be understood as meaning that each of the tackifier/mineral oil fraction is in each case below 1% by weight based on the hotmelt adhesive composition according to the invention.

Blending

The hotmelt material according to the invention may be made by mixing the SBC with the amorphous polyolefin (e.g. propylene-based polymer), and any other ingredients, as is known in the art for example using a co-rotating twin-screw extruder at an adapted processing temperature, for example between 200° C. and 250° C.

Hotmelt materials having the described features combine good processability, brought about by the low melt viscosity thereof, with exceptional mechanical properties. These combinations of the properties described qualify the hotmelt materials according to the invention for use thereof as high-performance hotmelt adhesives.

EXAMPLES

The following examples are given solely for the purpose of illustration and are not to be construed as limitations since many variations thereof are possible without departing from the scope of the absorbent article described herein. All values in weight percent, unless indicated otherwise.

The chemical, physical and mechanical properties of the ingredients used to formulate the adhesive are indicated in the Tables below.

A) SBC

TABLE 1

|  | Kraton MD 1648 | Kraton MD6951 | Kraton MD 1653 | Kraton G1730 | Kraton G 1657 | DZBH 506 |
|---|---|---|---|---|---|---|
| Melting enthalpy [J/g] | 0 | 0 | 0 | 0 | 0 | 0 |
| Elongation at break [%] | 750 | 750 | 600 | 800 | 750 | 900 |
| Strength [MPa] | 11 | 18 | 48 | 20 | 23 | 5 |
| Melt flow rate MFR (230° C./2.16 kg [g/10 min]) | 220 | 48 | 27 | 11* | 22* | 5 |

TABLE 1-continued

|  | Kraton MD 1648 | Kraton MD6951 | Kraton MD 1653 | Kraton G1730 | Kraton G 1657 | DZBH 506 |
|---|---|---|---|---|---|---|
| Styrene content (% by weight) | 20 | 34 | 30 | 20 | 13 | 13 |
| Iodine number [g of $I_2$/100 g of polymer] | 3.65 | 3.0 | 1.45 | 2.85 | 2.65 | 37 |
| $M_w$ [g/mol] | 73,500 | 133,300 | 64,060 | 103,300 | 104,600 | 167,300 |
| Type | Triblock SEBS | Triblock SEBS | Triblock SEBS | Triblock SEPS | Triblock SEBS | Triblock SEBS |

*At 5 kg

B) Amorphous Polyolefin

A suitable commercial propylene copolymer (PbP) material is indicated in Table 2 below.

TABLE 2

|  | Licocene PPA 330, a PbP |
|---|---|
| Catalysis method used for production | Metallocene catalysis |
| Melt viscosity @170° C. [mPas] | 200 |
| Propylene content [% by weight] | 79.5 |
| $M_W$ [g/mol] | 6,400 |
| PDI | 1.5 |
| $T_G$ [° C.] | −44 |
| Enthalpy of fusion [J/g] | 0 |
| Pour point: [° C.] | 21 |

C) PbP-g-ST or PbP-g-MA Polymer

Synthesis Example 1

2500 g of the propylene copolymer according to Table 2 were heated to 165° C. in a glass apparatus equipped with stirrer, internal thermometer and distillation bridge under nitrogen atmosphere. Over 3 hours 250 g of freshly distilled styrene was added continuously from a dosing funnel, while simultaneously adding from a second dropping funnel the continuous addition 25 g of di-tert.-butyl peroxide. After the end of the dosage, the reaction was allowed to continue for 1 hour. Subsequently a vacuum of about 20 mbar was applied to remove the volatile components A light-coloured pasty-liquid polymer was received showing the properties listed in Table 3.

TABLE 3

|  | PbP-g-ST | PbP-g-MA (Maleic anhydride-grafted Licocene ® PPA 330) |
|---|---|---|
| Catalysis method used for production of polymer backbone | Metallocene catalysis | Metallocene catalysis |
| Styrene or Maleic anhydride content [% by weight] | 10 | 1 |
| Melt viscosity @170° C. [mPas] | 280 | 255 |
| Propylene content on PbP backbone [% by weight] | 79.5 | 79.5 |
| Mw [g/mol] | 9240 | 6120 |
| PDI | 1.9 | 1.6 |

TABLE 3-continued

|  | PbP-g-ST | PbP-g-MA (Maleic anhydride-grafted Licocene ® PPA 330) |
|---|---|---|
| Tg [° C.] | −44 | −43.2 |
| Melting enthalphy [J/g] | 0 | 0 |
| Pour point: [° C.] | 45 | 35° C. |

D) Tackifier

The following commercially available tackifiers were used in the exemplary formulations:

a) Regalite 9100 (a hydrogenated C9, aromatic resins from Eastman);

b) Sukorez SU400 (a hydrogenated C5/cyclic/aromatic hydrocarbon resin from Kolon).

Blending

Melt mixtures of the components were produced by melt extrusion from the polymers described in Tables 1 and 2, optionally the tackifier and optionally further additives, in particular antioxidants. This was achieved using a co-rotating twin-screw extruder at a speed of 130 rpm and a processing temperature of 230° C.

The following antioxidants were added to produce the thermoplastic moulding materials:

Antioxidant 1: Hostanox®, a sterically hindered phenol, manufactured by Clariant; Antioxidant 2: Hostavin®, a hindered amine light stabilizer (HALS), manufactured by Clariant.

Desirable Properties

The following properties were determined from the hot-melt adhesive compositions thus produced:

melt viscosity at 170° C., elongation at break in [° %]

resilience [%].

To ensure the sprayability of the hotmelt adhesive, its melt viscosity at 170° C. should be less than or equal to 30,000 mPas. The following scheme is used to classify the other mechanical properties:

| Classification | Inadequate (C) | Sufficient (B) | Preferred (A) |
|---|---|---|---|
| Elongation at break | X < 800% | 800% ≤ X < 1000% | X ≥ 1000% |
| Resilience | X < 70% | 70% ≤ X < 90% | X ≥ 90% |

Working examples (inventive) —all amounts in weight %

TABLE 4

| | Ex. 1 | Ex. 2 | Ex. 3 | Ex. 4 | Ex. 5 | Ex. 6 | Ex. 7 | Ex. 8 |
|---|---|---|---|---|---|---|---|---|
| Licocene PPA 330 (PbP-ng) | 25 | 30 | 30 | 30 | 24 | 22 | 64.4 | 50.5 |
| PbP-g-ST | | | | | | | | |
| PbP-g-MA | | | | | | | | |
| Kraton MD1648 | 40 | | | 12.5 | 36 | 33 | | |
| Kraton MD 6951 | | 25 | | | | | 27.7 | 27.7 |
| Kraton MD 1653 | | | 25 | 12.5 | | | | |
| Kraton G1730 | | | | | | | 6.9 | 6.9 |
| Kraton G 1657 | | | | | | | | |
| DZBH 506 | | | | | | | | |
| Regalite 9100 | | 44.3 | 44.3 | | | | | |
| Sukorez SU400 | 34.3 | | | 44.3 | 39.3 | 44.3 | | 13.9 |
| Antioxidant 1 | 0.5 | 0.5 | 0.5 | 0.5 | 0.5 | 0.5 | 0.7 | 0.7 |
| Antioxidant 2 | 0.2 | 0.2 | 0.2 | 0.2 | 0.2 | 0.2 | 0.3 | 0.3 |
| Melt viscosity @ 170° C. [mPa · s] | 4,205 | 4,509 | 3,212 | 3,290 | 3,400 | 2,710 | 3,500 | 7,000 |
| Elongation at break [%] | 1,052 | 1,487 | 1,005 | 1,161 | 1,001 | 1,201 | 1,103 | 1,304 |
| (Classification) | (A) | (A) | (A) | (A) | (A) | (A) | (A) | (A) |
| Resilience at 300% [%] | 98.5 | 98.5 | 98.5 | 98.2 | 98.5 | 99.7 | 97.6 | 98.2 |
| (Classification) | (A) | (A) | (A) | (A) | (A) | (A) | (A) | (A) |
| Tensile strength [MPa] | 5.8 | 6.9 | 6.8 | 5.8 | 4.8 | 5.0 | 2.8 | 5.4 |

| | Ex. 9 | Ex. 10 | Ex. 11 | Ex. 12 | Ex. 13 | Ex. 14 | Ex. 15 | Ex. 16 |
|---|---|---|---|---|---|---|---|---|
| Licocene PPA 330 (PbP-ng) | 50 | 69.3 | 54.5 | 30 | 34.7 | 59.4 | | 34.6 |
| PbP-g-ST | | | 9.9 | | 29.7 | | 69.3 | 34.7 |
| PbP-g-MA | | | | | | | | |
| Kraton MD1648 | | | | 25 | | | | |
| Kraton MD 6951 | | | 27.7 | | 27.7 | 36.6 | | |
| Kraton MD 1653 | | | | | | | | |
| Kraton G1730 | | | 6.9 | | 6.9 | 3 | | |
| Kraton G 1657 | | | | | | | 29.7 | |
| DZBH 506 | 25.0 | 29.7 | | | | | | 29.7 |
| Regalite 9100 | | | | | | | | |
| Sukorez SU400 | 24 | | | 44.3 | | | | |
| Antioxidant 1 | 0.7 | 0.7 | 0.7 | 0.5 | 0.7 | 0.7 | 0.7 | 0.7 |
| Antioxidant 2 | 0.3 | 0.3 | 0.3 | 0.2 | 0.3 | 0.3 | 0.3 | 0.3 |
| Melt viscosity @170° C. [mPa · s] | 9,000 | 29,000 | 5,500 | 1,400 | 11,000 | 10,000 | 10,750 | 3,700 |
| elongation at break [%] | 1,247 | 885 | 882 | 1,189 | 950 | 942 | 1,049 | 1,156 |
| (Classification) | (A) | (B) | (B) | (A) | (B) | (B) | (A) | (A) |
| Resilience at 300% [%] | 99.4 | 99.4 | 97.6 | 95.5 | 98.5 | 98.9 | 98.2 | 97.8 |
| (Classification) | (A) | (A) | (A) | (A) | (A) | (A) | (A) | (A) |
| Tensile strength [MPa] | 2.6 | 0.7 | 1.7 | 3.6 | 1.8 | 1.3 | 2.4 | 3.8 |

| | Ex. 17 | Ex. 18 | Ex. 19 | Ex. 20 | Ex. 21 | Ex. 22 | Ex. 23 | Ex. 24 |
|---|---|---|---|---|---|---|---|---|
| Licocene PPA 330 (PbP) | | 54 | 49 | | 30 | 30 | 25 | 30 |
| PbP-g-St | 64.4 | | | | | | | |

TABLE 4-continued

| | | | | | | | | |
|---|---|---|---|---|---|---|---|---|
| PbP-g-MA | | 10 | 10 | 64 | | | | |
| Kraton MD1648 | | | | | | | | |
| Kraton MD 6951 | 27.7 | 28 | 40 | 28 | | | 5 | 5 |
| Kraton MD 1653 | | | | | 25 | | 20 | 20 |
| Kraton G1730 | 6.9 | 7 | | 7 | | 25 | | |
| Kraton G 1657 | | | | | | | | |
| DZBH 506 | | | | | | | | |
| Regalite 9100 | | | | | | | | |
| Sukorez SU400 | | | | | 44 | 44 | 49 | 44 |
| Antioxidant 1 | 0.7 | 0.7 | 0.7 | 0.7 | 0.5 | 0.5 | 0.5 | 0.5 |
| Antioxidant 2 | 0.3 | 0.3 | 0.3 | 0.3 | 0.5 | 0.5 | 0.5 | 0.5 |
| Melt viscosity @170° C. [mPa · s] | 3,500 | 10,750 | 3,700 | 18,000 | 3,000 | 9,300 | 3,600 | 3,900 |
| elongation at break [%] | 831 | 1,049 | 1,156 | 1,120 | 950 | 1,200 | 960 | 930 |
| (Classification) | (B) | (A) | (A) | (A) | (B) | (A) | (B) | (B) |
| Resilience at 300% [%] | 97.8 | 98.2 | 97.8 | 98.3 | 97.3 | 98.9 | 97.3 | 96.9 |
| (Classification) | (A) | (A) | (A) | (A) | (A) | (A) | (A) | (A) |
| Tensile strength [MPa] | 2.9 | 2.4 | 3.8 | 2.1 | 6.8 | 5.3 | 4.9 | 4.0 |

The examples of the invention have a melt viscosity at 170° C. of less than 30,000 mPas, and no (C) classification. Additional properties were further measured as compiled in the Table below:

TABLE 5

| | Desired properties | Ex. 1 | Ex. 2 | Ex. 3 | Ex. 4 | Ex. 5 | Ex. 6 | Ex. 9 |
|---|---|---|---|---|---|---|---|---|
| Storage Modulus @100° C. [Pa] | >200 Pa | 6,530 | 17,992 | 26,800 | 1,370 | 2,380 | 865 | 9,390 |
| tan δ @ 100° C. | <5 | 2.7 | 0.6 | 1.0 | 4.5 | 4.3 | 6.9 | 0.72 |
| Yield Stress @ 23° C. [MPa] | <2 MPa | 0.09 | 0.06 | 0.09 | 0.06 | 0.09 | 0.10 | 0.02 |
| True Strain at Break @ 23° C. | >2.2 | 2.8 | 3.5 | 2.6 | 2.8 | 2.9 | 2.9 | 2.9 |
| Strain Hardening Index @ 23° C. | >25 | 591 | 2,010 | 473 | 550 | 597 | 568 | 663 |

| | Desired properties | Ex. 10 | Ex. 12 | Ex. 13 | Ex. 14 | Ex. 15 | Ex. 16 |
|---|---|---|---|---|---|---|---|
| Storage Modulus @100° C. [Pa] | >200 Pa | 5,338 | 192 | 7,452 | 3,187 | 12,352 | 1,500 |
| tan δ @ 100° C. | <5 | 1.08 | 10.88 | 0.66 | 0.95 | 0.88 | 0.88 |
| Yield Stress @ 23° C. [MPa] | <2 MPa | 0.02 | 0.09 | 0.03 | 0.04 | 0.03 | 0.002 |
| True Strain at Break @ 23° C. | >2.2 | 3.1 | 2.8 | 2.9 | 3.4 | 2.9 | 2.2 |

TABLE 5-continued

| | | | | | | | |
|---|---|---|---|---|---|---|---|
| Strain Hardening Index @ 23° C. | >25 | 650 | 315 | 123 | 128 | 302 | 209 |

| | Desired properties | Ex. 21 | Ex. 22 | Ex. 23 | Ex. 24 |
|---|---|---|---|---|---|
| Storage Modulus @100° C. [Pa] | >200 Pa | 26,481 | 10,874 | 3,792 | 6,090 |
| tan δ @ 100° C. | <5 | 1.0 | 1.4 | 2.9 | 2.2 |
| Yield Stress @ 23° C. [MPa] | <2 MPa | 0.06 | 0.06 | 0.19 | 0.13 |
| True Strain at Break @ 23° C. | >2.2 | 2.52 | 3.35 | 2.75 | 2.76 |
| Strain Hardening Index @ 23° C. | >25 | 467 | 1265 | 384 | 313 |

Tables 4 and 5 show additional mechanical properties which are important for the application as stable fibrous net structures. The parameters of importance, namely Yield Stress, the True Strain at Break and the Strain Hardening Index fulfil all requirements for mechanical stability of spray web applications. By this the material does not fail instantly at high local stresses, which leads to a significant increase of net structure extensibility.

Comparative Examples (Non-Inventive) —all Amount in Weight %

The comparative examples 1-3 are formulated with semi-crystalline polyolefins (Licocene 2502, Licocene 1302) instead of the amorphous polyolefins, and comparative examples 4-7 are formulated without SBC.

TABLE 6

| | Comp. Ex. 1 | Comp. Ex. 2 | Comp. Ex. 3 | Comp. Ex. 4 | Comp. Ex. 5 | Comp. Ex. 6 | Comp. Ex. 7 |
|---|---|---|---|---|---|---|---|
| Licocene 2502 | 50 | 40 | | 69 | | | 59 |
| Licocene 1302 | | | 40 | | | | |
| Licocene PPA 330 | | | | | 59 | 50 | 10 |
| Vistamaxx 6502 | | | | 30 | 40 | 49 | 30 |
| Kraton MD 1648 | 49 | 59 | 59 | | | | |
| Kraton G 1657 | | | | | | | |
| Antioxidant 1 | 0.7 | 0.7 | 0.7 | 0.7 | 0.7 | 0.7 | 0.7 |
| Antioxidant 2 | 0.3 | 0.3 | 0.3 | 0.3 | 0.3 | 0.3 | 0.3 |
| Melt viscosity @ 170° C. [mPa · s] | 70,000 | 116,000 | 30,860 | 27,060 | 8,252 | 11,040 | 11,110 |
| Tensile strength [MPa] | 6.1 | 4.9 | 3.7 | 11.0 | 1.1 | 1.5 | 11.0 |
| Elongation at break [%] | 815 | 635 | 666 | 1,250 | 328 | 419 | 1,121 |
| (Classification) | (B) | (C) | (C) | (A) | (C) | (C) | (A) |
| Resilience at 300% [%] | 76.3 | 89.7 | 94.1 | 26.5 | 76.5 | 75.0 | 45.6 |
| (Classification) | (B) | (B) | (A) | (C) | (B) | (B) | (C) |

The inventive examples show significantly better values for the critical mechanical properties in comparison to the comparative examples. The hotmelt of the invention combine a low melt viscosity with a high elongation at break and a high resilience. Only the inventive examples have both a sufficiently low melt viscosity as well as reasonable elongation at break as well as adequate resilience to be suitable for achieving sprayable fibrous web applications.

Measurement Methods

All official test methods (ISO, DIN, etc.) are conducted using the latest test version available at the filing date of the application, unless otherwise indicated.

Weight-Average Molecular Weight of the Propylene-Based Polymer

The determination of the weight-average molecular weights Mw of the propylene-based polymers is carried out in 1,3-ortho-dichlorobenzene and determined with a PP calibration. The measurement is carried out by gel permeation chromatography at a temperature of 135° C. The determination is carried out in accordance with ISO 16014-1.

Melt Viscosity (e.g. at 170° C.)

The determination of the melt viscosity was carried out according to the standard DIN 53019.

Weight-Average Molecular Weight of the SBC

Determination of the weight-average molecular weights $M_w$ of the SBC is conducted in THF as a mobile phase at a flow rate of 1 mL/min with a polystyrene calibration with standards in the range of 680-1 670 000 g/mol. Measurement are carried out by gel permeation chromatography on styrene-divinylbenzene copolymer columns from PSS at a constant temperature of 40° C. For measurement a SBC polymer solution us prepared in a concentration of (2 mg Polymer)/(ml THF) and 50 µL of the solution is injected. A differential refractometer is used for detection.

Pour Point

The pour point is determined according to the standard ASTM D97.

Iodine Number

The Iodine number is determined according to the standard DIN 6162 (version 2014).

Polydispersity Index

The polydispersity index PDI is calculated from the quotient of weight-average molecular weight $M_w$ and number-average molecular weight $M_n$ and was determined according to the standard ISO 16014-1.

Mechanical Properties

The (tensile) strength ("Zugsfestigkeit") and elongation at break ("Bruchdehnung") of the hotmelt materials are determined according to ISO 527 save that in this case a non-standard test specimen produced by hotmelt pressing and differing from the test specimen conforming to the standard in terms of its dimensions was used. The test specimens used for measuring strength and elongation at break have the following dimensions (see also FIG. 8): total length: 50 mm, width of narrow part: 3.3 mm, width at ends: 7 mm, length of narrow parallel part: 25 mm, thickness: 1 mm.

The resilience of hotmelt materials is tested with the aforementioned test specimens on a tensile/elongation machine from Zwick, by stretching a test specimen of the sample to be determined of starting length L1 by 300% to length L2, at an elongation rate of 50 mm/min. Subsequently, the test specimen was allowed to fully relax, i.e. the test specimen no longer changed its length at a force of 0 Pa. The resulting length corresponds to L3.

The resilience R in % is given as follows: R=((L2−L3)/L2−L1)*100

Enthalpy of Fusion Test Method

The enthalpy of fusion is measured as indicated in ISO 11357-2 (2013).

Fusion Index Test Method

The fusion index is determined by the measurement specified by ASTM D3418-08 "Standard Test Method for Transition Temperatures and Enthalpies of Fusion and Crystallization of Polymers by Differential Scanning Calorimetry." To determine a material's fusion index, the material's enthalpy of fusion, expressed in Joules/gram as measured according ASTM D3418, shall be divided by 208 J/g. For example, the fusion index of a polypropylene with an experimentally determined enthalpy of fusion of 100 J/g is calculated as (100/208)*100%=48.1%. Another example: the fusion index of PE with an experimentally determined enthalpy of fusion of 30 J/g is calculated as (30/208)*100%=14.4%.

Glass Transition Temperature Test Method

The glass transition temperature is determined by the measurement specified by ASTM D3418-15 "Standard Test Method for Transition Temperatures and Enthalpies of Fusion and Crystallization of Polymers by Differential Scanning Calorimetry."

Oscillatory Rheometry Test Method

The Oscillatory Rheometry Test Method is used to measure the Storage Modulus and the Loss Factor of a polymer composition. A controlled-stress rotational rheometer (such as Discovery HR-3, TA Instruments, New Castle, DE, USA, or equivalent) capable of sample temperature control (using a Peltier cooler and resistance heater combination) with a precision equal to or exceeding 0.5° C. over at least the range of −10° C. to 150° C. The rheometer is operated in a parallel plate configuration with 20-mm stainless steel parallel-plate tooling.

A parallel plate gap of 1000 µm is initially used in the method. To compensate for thermal expansion of the tooling, the gap is set to 1000 µm, and a mapping of actual plate gap (as measured using a suitable standard test fluid) a function of temperature over the range −10° C. to 150° C. is performed. This mapping is then used throughout the determination of the Storage Modulus Parameter and the Loss Factor Parameter.

The rheometer is heated to 150° C., the polymer composition is introduced in the rheometer, the gap is set to 1050 m, excess protruding sample is trimmed, and the gap is then set to 1000 µm. (The axial force control of the rheometer is set to 0 N and be maintained within ±0.1 N of force during the experiment, thereby thermal expansion/contraction of the sample itself is compensated by adjusting the gap in order to avoid overfilling or underfilling in addition to the abovementioned compensation of the tooling.) The rheometer is then allowed to cool to 130° C., at which point the measurement commences with temperature ramped from 130° C. to −10° C. at a constant rate of cooling of 2° C./min. The applied strain amplitude is 0.1%, and the frequency of oscillation is 1 Hz (that is, one cycle per second). The resulting oscillatory stress is recorded.

After this step, the sample temperature is set to 23° C. (temperature is ramped to this setpoint at a rate of 10° C./min), and the sample is allowed to rest for 4.0 hours at 23° C. At the end of this period, the temperature is set to −10° C. (temperature is ramped to this setpoint at a rate of 10° C./min), the sample is equilibrated for 300 seconds at −10° C., and a second oscillatory rheology measurement is conducted (0.1% strain, frequency of oscillation of 1 Hz) while temperature is ramped upward to 130° C. at a constant rate of increase of 2° C./min.

From the first decreasing temperature sweep, the storage modulus G' is calculated and recorded at 100° C., and these values are reported in Pascals (Pa) to the nearest 1 Pa as the "Storage Modulus at 100° C.". From the first, decreasing temperature sweep, the loss factor (also known as tan delta) is calculated recorded at 100° C., and this dimensionless value is reported to the nearest hundredth as the "Loss Factor at 100° C.". The storage modulus G' can also be calculated and recorded at different temperatures, such as 25° C.

Extensional Test Method

The Extensional Test Method is used to determine the Yield Stress Parameter, the Max Stress Parameter, the Strain to Break Parameter, and the Strain Hardening Index for a specimen of a polymer composition. A thin film specimen formed of polymer composition is analyzed with a rotational rheometer fitted with a specialized fixture with counter rotating rollers, and the stress associated with extensional strain imparted is measured and recorded.

Instrumental Setup

A controlled-strain rotational rheometer (ARES G2, TA Instruments, New Castle, DE, USA, or equivalent) is fitted with a fixture that has counter rotating cylindrical rollers specifically designed for the interrogation of extension deformation of films. An example of a suitable fixture is the Extensional Viscosity Fixture, or EVF (EVF, TA Instruments, or equivalent). The rheometer is further fitted with a forced-convection oven FCO (FCO, TA Instruments, or equivalent) and cooling system (ACS 2, TA Instruments, or equivalent) capable of controlling temperate from at least −50 to 250° C. to a within a tolerance of 0.5° C.

Specimen Preparation

Approximately 10 g of the polymer composition is placed in a polytetrafluoroethane (PTFE) bowl and introduced into a vacuum oven. After 15 minutes at 200° C. at ambient pressure, the pressure is lowered to 10 mbar, and the polymer composition is subsequently held at 200° C. and at 10 mbar for 45 minutes to remove air bubbles from the polymer composition. The polymer composition is removed from the vacuum oven and allowed to cool to ambient lab conditions (23±2° C.) for 90±30 minutes, at which point the polymer composition is removed from the PTFE bowl and placed between 2 sheets of siliconized paper. A metal shim 0.50 mm in thickness is used in the heated press as a spacer to obtain a film thickness of 0.50 mm when pressed with a heated press at 90° C. and 10 Bar (instrument setting) for 60 seconds to a polymeric film. If 90° C. is insufficient to melt the polymer composition, a higher temperature (but the lowest temperature sufficient to melt the composition) is used. The film is stored at least 120 hours in the laboratory at 23±2° C. prior to testing. From the film individual specimens for measurement are punched with a sample cutter to the specimen dimensions of 20.0 mm by 10.0 mm by 0.50 mm. The exact thickness will be determined with a digital caliper (Electronic Caliper PRO-MAX Fowler) to the nearest of 0.01 mm and entered into the rheometer software.

Measurement

The siliconized paper is removed and the specimen of polymer composition is briefly pressed onto the cylinder surface to attach the film to the cylinders of the EVF. The specimen is placed perpendicular to the axis of rotation of the cylinders.

The specimen mounted on the EVF is then placed in the forced convection oven of the rheometer for thermal conditioning and is kept isothermal at 23±0.5° C. for 120±10 s. After this time has elapsed, the specimen is mechanically conditioned. To mechanically condition the specimen, the torque transducer is zeroed, and the sample is put under a pre-stretch rate of 0.001 s−1 for 0.30 s and then allowed to relax for 60 s. (In this method, all strain is expressed in terms of Hencky strain, also known as "true strain" or "logarithmic strain.") The measurement is performed in the FCO oven at 23° C.±0.5° C. The strain rate extension for the measurement is 0.01 s−1, and the strain at maximum extension is 4.0. After measurement, the specimen is checked for rupturing. If it has ruptured, the location of the break is noted. If the rupture is approximately in the middle between the two cylinders of the EVF, the data collected are deemed acceptable. Otherwise, if the polymeric film break is at or close to the rotating cylinders, the results are discarded and the measurement performed again on a replicate specimen.

Analysis

For the extensional stress calculation, a constant volume is assumed. From the raw torque versus angular displacement data recorded by the rheometer, extensional stress (in megapascals, or MPa) versus Hencky strain data are calculated. The data are plotted in semi-logarithmic fashion with Hencky strain on the abscissa (linear scale) and extensional stress on the ordinate (logarithmic scale). A linear fit with a positive slope with an $R^2$ value of 0.9 or greater is set between a Hencky strain of 0.5 and 1. Otherwise, the maximum value of extensional stress recorded during the measurement is reported as the Yield Stress Parameter, again reported in MPa to the nearest kilopascal. The value of the fitted line at a Hencky strain of zero (that is, the y-intercept), is defined as the Yield Stress Parameter, which is reported in MPa to the nearest kilopascal. The maximum stress value in the plot is defined as the Maximum Stress Parameter, which is reported in MPa to the nearest kilopascal. The Hencky Strain, when the specimen ruptures and/or the reported torque value is lower than 100 μNm, is reported as Strain to Break Parameter as dimensionless value to the nearest of 0.1 (or, in the case it did not rupture during the measurement, to a strain of 4.0). The difference of the Maximum Stress and the Yield Stress divided by the Yield Stress is defined as Strain Hardening Index, which is reported as dimensionless value to the nearest of 1.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article for personal hygiene comprising a hotmelt adhesive, wherein the hotmelt adhesive comprises
    from 20% to 45% by weight of the hotmelt adhesive of at least one styrene-block-copolymer (SBC) and
    from 10% to 60% by weight of the hotmelt adhesive of at least one amorphous polyolefin having an enthalpy of fusion of less than 10 J/g,
    wherein the hotmelt adhesive does not comprise any polyolefin having an enthalpy of fusion greater than 10 J/g,
    wherein enthalpy of fusion is measured in accordance with ISO 11357-2 (2013).

2. The absorbent article according to claim 1, wherein the hotmelt adhesive further comprises at least one tackifier, and wherein:
    the tackifier amount is of from 10% to 60%, by weight of the hotmelt adhesive.

3. The absorbent article according to claim 1, wherein the hotmelt adhesive comprises less than 10% of a tackifier.

4. The absorbent article according to claim 1, wherein the SBC comprises an elastomeric block copolymer selected from the group consisting of elastomeric triblock copolymers of the ABA type; elastomeric diblock copolymers of the AB type; and elastomeric multiblock copolymers of the type [AB]n, wherein n is the number of blocks; wherein A designates rigid styrene units and B designates elastomeric units.

5. The absorbent article according to claim 1, wherein the SBC comprises one or more hydrogenated polymers selected from the group of styrene-ethylene-butadiene-styrene (SEBS), styrene-ethylene-propylene-styrene (SEPS) and styrene-ethylene-propylene (SEP) polymers.

6. The absorbent article according to claim 1, wherein the SBC has a styrene content of 10% to 40% by weight of the SBC.

7. The absorbent article according to claim 1, wherein the hotmelt adhesive comprises at least one propylene-based polymer (PbP) as the amorphous polyolefin.

8. The absorbent article according to claim 7, wherein the at least one PbP comprises a propylene-based polymer backbone having a weight-average molecular weight of less than 10,000 g/mol.

9. The absorbent article according to claim 8, wherein the at least one PbP is grafted with 1% to 50% by weight, based on the weight of PbP-backbone, of vinyl-aromatic monomers (PbP-g-VAM).

10. The absorbent article according to claim 9, wherein the vinyl-aromatic monomers comprise styrene and its derivatives (PbP-g-ST).

11. The absorbent article according to claim 7, wherein at least one PbP is grafted with 0.1% to 20% by weight, based on the weight of PbP-backbone, of unsaturated vinyl monomers including a heteroatom (PbP-g-UVMH).

12. The absorbent article according to claim 11, wherein the unsaturated vinyl monomers comprise maleic anhydride (PbP-g-MA).

13. The absorbent article according to claim 1, wherein the amorphous polyolefin comprises a grafted propylene-based polymer and a non-grafted propylene-based polymer, wherein the grafted and non-grafted propylene-based polymers have the same polymer backbone.

14. The absorbent article according to claim 7, wherein the at least one PbP is a copolymer of propylene and ethylene, and wherein the copolymer is derived from 60% to 85% by weight propylene and from 15% to 40% by weight ethylene.

15. The absorbent article according to claim 1, wherein the amorphous polyolefin has an enthalpy of fusion of less than 5 J/g.

16. The absorbent article according to claim 15, wherein the amorphous polyolefin has an enthalpy of fusion of 0 J/g.

17. The absorbent article according to claim 1, wherein the hotmelt adhesive has at least one of the properties selected from:
    a melt viscosity at 170° C., measured in accordance with DIN 53019, in the range of 100 mPas to 30,000 mPas;
    an elongation at break of more than 800%, measured in accordance with ISO 527 with the exception that the test specimen has the following dimensions deviating from the standard: total length: 50 mm, width of narrow part: 3.3 mm, width at ends: 7 mm, length of narrow parallel part: 25 mm, thickness: 1 mm;
    a resilience R of more than 70%, measured with a resilience test in which the test specimen is stretched on a tensile/elongation machine by 300% of the starting length L1 to length L2 at an elongation rate of 50 mm/min and subsequent full relaxation to relaxed length L3, whereby the resilience R was calculated according to the formula R=((L2−L3)/L2−L1)*100 and the test specimen has the following dimensions: total length: 50 mm, width of narrow part: 3.3 mm, width at ends: 7 mm, length of narrow parallel part: 25 mm, thickness: 1 mm;
    a strain at break higher than 2.2;
    a strain hardening index higher than 25;
    a Storage Modulus at 100° C. of more than 200 Pa, as measured by the Oscillatory Rheometry Test Method;
    a Storage Modulus at 25° C. of less than $1.2 \times 10^9$ Pa, as measured by the Oscillatory Rheometry Test Method;
    a tan δ@100° C.<5, as measured by the Oscillatory Rheometry Test Method.

18. The absorbent article according to claim 1, wherein the hotmelt adhesive bonds at least two components of the absorbent article, wherein the components are selected from film components, nonwoven components, superabsorbent particles, and elastic components.

19. The absorbent article according to claim 1, wherein the hotmelt adhesive is in the form of a fibrous network that immobilizes superabsorbent particles on a substrate.

* * * * *